(12) United States Patent
Maracaja

(10) Patent No.: US 11,000,657 B2
(45) Date of Patent: May 11, 2021

(54) RESPIRATORY APPARATUS FOR LUNG INJURY

(71) Applicant: Luiz Maracaja, San Antonio, TX (US)

(72) Inventor: Luiz Maracaja, San Antonio, TX (US)

( * ) Notice: Subject to any disclaimer, the term of this patent is extended or adjusted under 35 U.S.C. 154(b) by 161 days.

(21) Appl. No.: 15/934,249

(22) Filed: Mar. 23, 2018

(65) Prior Publication Data

US 2018/0272089 A1 Sep. 27, 2018

Related U.S. Application Data

(60) Provisional application No. 62/475,278, filed on Mar. 23, 2017.

(51) Int. Cl.
*A61M 16/04* (2006.01)
*A61B 1/00* (2006.01)
(Continued)

(52) U.S. Cl.
CPC ..... *A61M 16/0404* (2014.02); *A61B 1/00082* (2013.01); *A61B 1/00098* (2013.01); *A61B 1/00135* (2013.01); *A61B 1/00154* (2013.01); *A61B 1/015* (2013.01); *A61B 1/018* (2013.01); *A61B 1/042* (2013.01); *A61B 1/07* (2013.01); *A61B 1/126* (2013.01); *A61B 1/2676* (2013.01); *A61M 16/0431* (2014.02); *A61M 16/0434* (2013.01); *A61M 16/0459* (2014.02); *A61M 16/0463* (2013.01); *A61M 16/0833* (2014.02); *A61M 16/105* (2013.01); *A61M 2210/1035* (2013.01)

(58) Field of Classification Search
CPC . A61B 5/1076; A61M 16/00; A61M 16/0009; A61M 16/04; A61M 16/0404; A61M 16/0411; A61M 16/0427; A61M 16/0434; A61M 16/0459; A61M 16/0463; A61M 16/0479; A61M 16/0484; A61M 16/0486; A61M 16/0488; A61M 2025/1059; A61M 25/09; A61M 25/1011; Y10S 128/911; Y10S 128/912
See application file for complete search history.

(56) References Cited

U.S. PATENT DOCUMENTS 3,927,676 A  12/1975 Schultz
4,722,335 A   2/1988 Vilasi
(Continued)

FOREIGN PATENT DOCUMENTS

WO   WO 2006/072153   7/2006

OTHER PUBLICATIONS

Brodsky et al., "Tracheal Diameter Predicts Double-Lumen Tube Size: A Method for Selecting Left Double-Lumen Tubes" *Brief Communications* 1996, 861-864.
(Continued)

*Primary Examiner* — Annette Dixon

(57) ABSTRACT

Embodiments are directed to an endotracheal intubation system that provides for differential ventilation of lungs and lung lobes. Certain aspects are directed to an assembled device having three lumens: (1) a tracheal lumen that provides for ventilation of the upper lobes of the lung, (2) a first lobular lumen that provides for ventilation of a first lower lobe of the lung, and (3) a second lobular lumen that provides for ventilation of a second lower lobe of the lung.

4 Claims, 40 Drawing Sheets

(51) Int. Cl.
*A61B 1/267* (2006.01)
*A61M 16/10* (2006.01)
*A61B 1/018* (2006.01)
*A61B 1/07* (2006.01)
*A61B 1/04* (2006.01)
*A61B 1/12* (2006.01)
*A61M 16/08* (2006.01)
*A61B 1/015* (2006.01)

(56) References Cited

U.S. PATENT DOCUMENTS

| | | | | |
|---|---|---|---|---|
| 5,315,992 | A | * | 5/1994 | Dalton ............... A61M 16/04 128/207.15 |
| 5,359,999 | A | * | 11/1994 | Kinsman ............ A61H 31/00 128/204.21 |
| 5,660,175 | A | * | 8/1997 | Dayal ................. A61M 16/00 128/207.15 |
| 6,189,533 | B1 | | 2/2001 | Simon et al. |
| 6,443,156 | B1 | * | 9/2002 | Niklason ............ A61M 16/04 128/207.14 |
| 6,668,832 | B2 | | 12/2003 | Hipolito et al. |
| 2002/0185135 | A1 | * | 12/2002 | Amar .................. A61M 16/04 128/207.15 |
| 2008/0236590 | A1 | | 10/2008 | Reissmann |
| 2010/0313896 | A1 | | 12/2010 | O'Neil et al. |
| 2012/0024292 | A1 | | 2/2012 | Sandmore et al. |
| 2014/0230823 | A1 | | 8/2014 | Adams |

OTHER PUBLICATIONS

Chovancova, Michaela, and Jacob Elcner. "The Pressure Gradient in the Human Respiratory Tract." *EPJ Web of Conferences* published by EDP Sciences 2014, 67, 6 pages.

Saguil et al., "Acute Respiratory Distress Syndrome: Diagnosis and Management" *American Family Physician* 2012, 85(4), 352-358.

Shiotsuka et al., "A Quantitative Evaluation of Fluid Leakage around a Polyvinyl Chloride Tapered Endotracheal Tube Cuff Using an in-Vitro Model." *HSR Proceedings in Intensive Care & Cardiovascular Anesthesia*, EDIMES Edizioni Internazionali Srl, 2012.

* cited by examiner

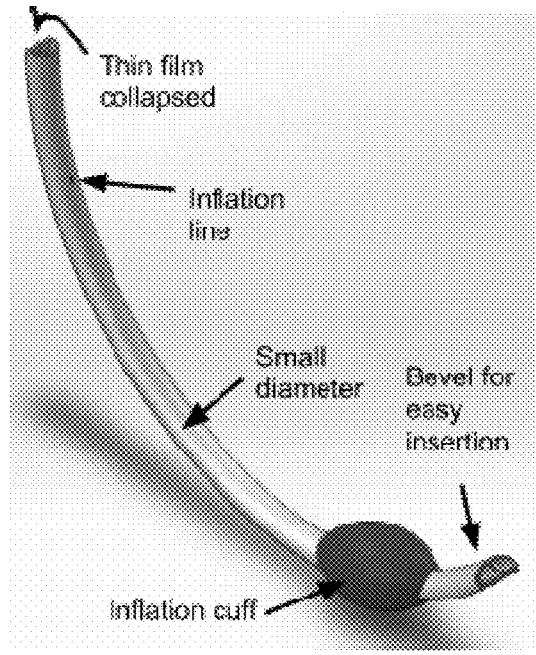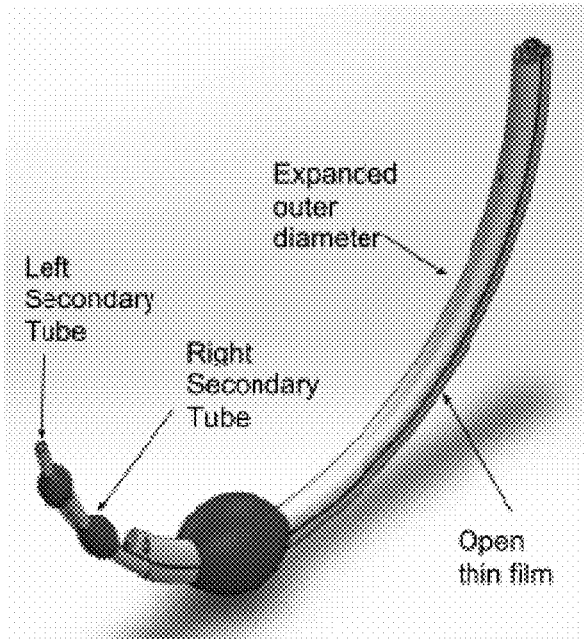
FIG. 19A  FIG. 19B
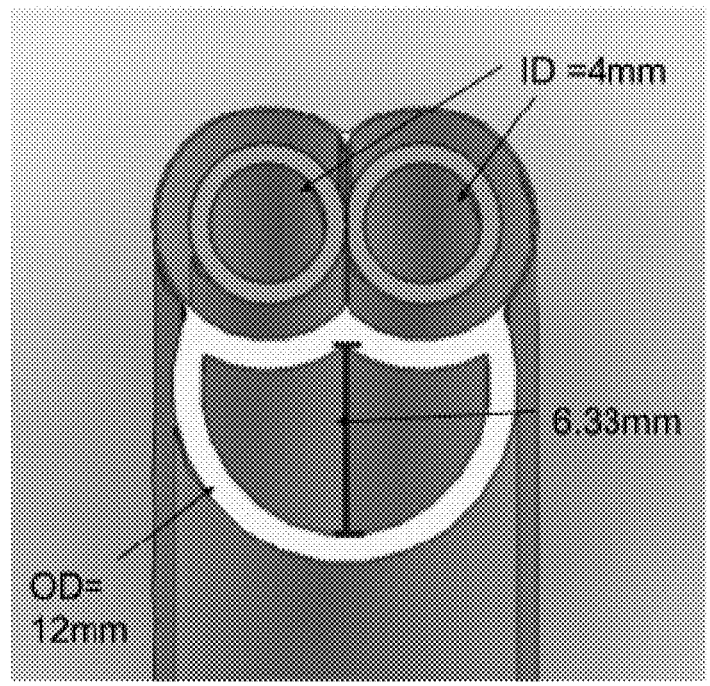
FIG. 20

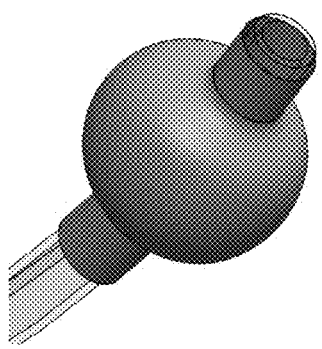
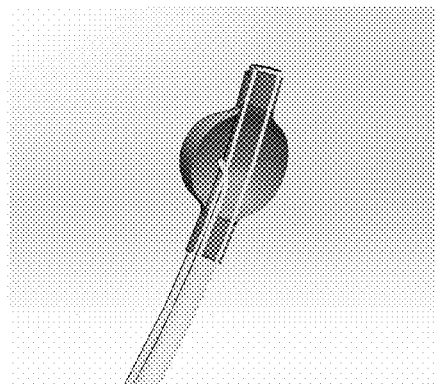
FIG. 25  FIG. 26
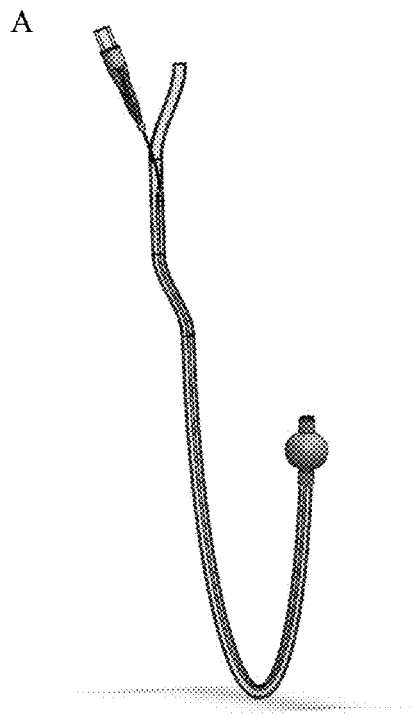
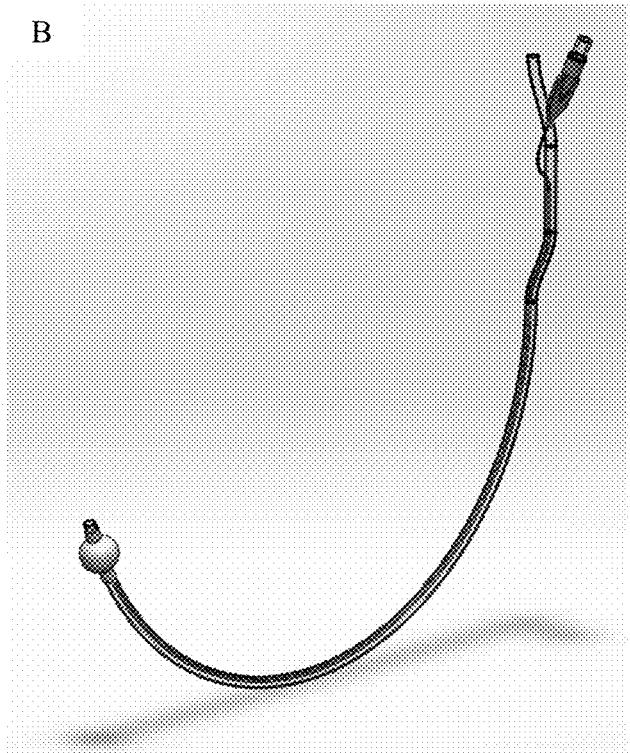
FIG. 27A  FIG. 27B

A  B

RESPIRATORY APPARATUS FOR LUNG INJURY

This application claims priority to U.S. Application No. 62/475,278, filed Mar. 23, 2017, which is incorporated here by reference in its entirety.

BACKGROUND

The acute diseases of the lung are life-threatening emergencies that cause respiratory failure. Respiratory failure is a syndrome in which the respiratory system fails to provide gas exchange function. Some examples of acute lung problems are cardiogenic or non-cardiogenic pulmonary edema, pneumonia, and massive pulmonary hemorrhage. A common characteristic of these pathologies is that they generally involve fluid filling or collapse of alveolar units.

Hemoptysis is the act of coughing up blood or blood-stained mucus from the bronchi, larynx, trachea, or lungs. This can occur with thoracic trauma, lung cancer, infections such as tuberculosis, bronchitis, or pneumonia, and certain cardiovascular conditions. Massive hemoptysis is a life-threatening condition. It is classically defined as more than 600 ml of blood from the tracheal bronchial tree over the period of 24 hours. Massive hemoptysis usually causes death by asphyxia and not by hypovolemia. Other acute respiratory pathologies such as acute pulmonary edema, near drowning can also course with massive amounts of alveoli fluid in similar manner. Hemoptysis can be diffuse or focal and the treatment is multidisciplinary based on the cause. Flexible or rigid bronchoscopy can be used for diagnosis and treatment for hemoptysis or similar conditions. Lung isolation with bronchial blockers or double lumen tube (DLT) are used to temporize bleeding until definitive treatment is available. For focal causes, lung resection and bronchial artery embolization are the most frequent modalities. The maintenance of patient oxygenation until definitive treatment is vital. Removal of the blood from the tracheal bronchial tree is necessary because the blood will flood the areas of the lung with normal aeration worsening the hypoxemia. However, to suction the blood from the tracheal bronchial tree it is necessary to interrupt the ventilation and disconnect the respiratory circuit. The disconnection and suction of the endotracheal tube will reduce the oxygenation in the lungs and causing hypoxia. Moreover, to recover from hypoxia, hyperventilation is normally attempted and that can stretch the bleeding source and increase the bleeding output. This cascade of events bleeding in the airway, hypoxia, suction, more hypoxia, hyperventilation causing overstretch and more bleeding will turn in to a vicious cycle with poor outcome. The most acceptable treatment that can potentially tamponade the bleeding is positive end expiratory pressure (PEEP) which provide counter pressure reducing the bleeding. However, applying PEEP is not feasible if the circuit needs to be disconnected frequently for blood suctioning. Close suction system is the most effective way to remove the blood from the airway with minimal decruitment of the alveoli. In massive hemoptysis, the bleeding high output can be difficult to control and overwhelming for the medical providers. Blood will reach, the limbs of the respiratory system, the capnograph line, and the ventilator valves if not removed on time, and the immediate need of a new of entire new respiratory set up may not be feasible in timely manner.

Acute Respiratory Distress Syndrome (ARDS) is a form of non-cardiogenic pulmonary edema provoked by an acute injury to the lungs that results in flooding of alveoli. Additional common findings in ARDS include partial collapse of the lungs (atelectasis) and low levels of oxygen in the blood (hypoxemia). However, in ARDS, these changes are not due to heart failure. The clinical syndrome is associated with pathological findings including pneumonia, eosinophilic pneumonia, cryptogenic organizing pneumonia, acute fibrinous organizing pneumonia, and diffuse alveolar damage.

ARDS may be triggered by various pathologies such as trauma, pneumonia and sepsis. The syndrome is associated with a high mortality rate between 20 and 50%. The mortality rate with ARDS varies widely based on severity, the patient's age, and the presence of other underlying medical conditions. The signs and symptoms of ARDS often begin within few hours of an inciting event. Signs and symptoms may include shortness of breath, fast breathing, and a low oxygen level in the blood. A chest x-ray frequently demonstrates generalized infiltrates or opacities in both lungs, which represent fluid accumulation in the lungs.

Common causes of ARDS include sepsis, pneumonia, trauma, multiple blood transfusions, lung contusion, aspiration of stomach contents, and drug abuse or overdose. Other causes of ARDS include burns, pancreatitis, near drowning, or the inhalation of chemical irritants such as smoke, phosgene, or chlorine gas. The hallmark of ARDS is diffuse injury to cells which form the alveolar barrier, surfactant dysfunction, activation of the innate immune response, and abnormal coagulation. In effect, ARDS results in impaired gas exchange within the lungs at the level of the microscopic alveoli. The triggering insult to the tissue usually results in an initial release of chemical signals and other inflammatory mediators secreted by local epithelial and endothelial cells. Neutrophils and some T-lymphocytes quickly migrate into the inflamed lung tissue and contribute in the amplification of the phenomenon.

Typical histological presentation involves diffuse alveolar damage and hyaline membrane formation in alveolar walls. Although the triggering mechanisms are not completely understood, recent research has examined the role of inflammation and mechanical stress. Inflammation, such as that caused by sepsis, causes endothelial dysfunction, fluid leakage from the capillaries and impaired drainage of fluid from the lungs. In a secondary phase, endothelial dysfunction causes cells and inflammatory exudate to enter the alveoli. This pulmonary edema increases the thickness of the alveolo-capillary space, increasing the distance the oxygen must diffuse to reach blood, which impairs gas exchange leading to hypoxia, increases the work of breathing and eventually induces fibrosis of the airspace. Edema and decreased surfactant production by type II pneumocytes may cause whole alveoli to collapse or to completely flood. This loss of aeration contributes further to the right-to-left shunt in ARDS. As the alveoli contain progressively less gas, the blood flowing through the alveolar capillaries is progressively less oxygenated, resulting in massive intrapulmonary shunting. The loss of aeration may follow different patterns depending upon the nature of the underlying disease and other factors. These are usually distributed to the lower lobes of the lungs, in their posterior segments, and they roughly correspond to the initial infected area.

In sepsis or trauma-induced ARDS, infiltrates are usually more patchy and diffuse. The posterior and basal segments are always more affected, but the distribution is even less homogeneous. Loss of aeration also causes important changes in lung mechanical properties that are fundamental in the process of inflammation amplification and progression to ARDS in mechanically ventilated patients. Persons with ARDS typically are short of breath, with arterial blood gas findings consistent with low oxygenation and imaging findings suggestive of a diffuse, alveolar infiltrative process.

According to the 2012 Berlin definition, ARDS is characterized by: lung injury of acute onset, within 1 week of an apparent clinical insult and with progression of respiratory symptoms; bilateral opacities on chest imaging (chest radiograph or CT) not explained by other lung pathology (e.g. effusion, pneumothorax, or nodules); respiratory failure not explained by heart failure or volume overload; decreased $PaO_2/FiO_2$ ratio (a decreased $PaO_2/FiO_2$ ratio indicates reduced arterial oxygenation from the available inhaled gas): mild ARDS: 201-300 mmHg (≤39.9 kPa); moderate ARDS: 101-200 mmHg (≤26.6 kPa), severe ARDS: ≤100 mmHg (≤13.3 kPa).

Note that the Berlin definition requires a minimum positive end expiratory pressure (PEEP) of 5 cm $H_2O$ for consideration of the $PaO_2/FiO_2$ ratio. This degree of PEEP may be delivered noninvasively with CPAP to diagnose mild ARDS.

Medical imaging is key to diagnosis. While a chest x-ray is often ordered as a first-line test, CT scanning showing a bilateral infiltrative process may also be helpful (FIG. 2). The diffuse and often nonspecific consolidation that is depicted on chest radiographs in patients with ARDS is, in fact, heterogeneous on CT scans. Also, CT scans show that the parenchymal consolidation in ARDS is in the gravity-dependent areas of the lung. Therefore, the disease is not as diffuse as the chest radiograph findings alone suggest. Chest CT scans findings in patients with ARDS revealed the following findings: Bilateral abnormalities in almost all the patients, predominantly dependent abnormalities (86%); Patchy abnormalities (42%); Homogeneous abnormalities (23%); Ground-glass attenuation (8%); Mixed ground-glass appearance and consolidation (27%); Basilar predominant abnormalities (68%); Areas of consolidation with air bronchograms (89%). ARDS that is due to pulmonary disease tends to be asymmetrical, with a mix of consolidation and ground-glass opacification, whereas ARDS that is due to extrapulmonary causes has predominantly symmetric ground-glass opacification. In the later stages of ARDS, CT scanning is more reliable than the chest radiograph in the detection of suspected fibrosis as the changes that accompany fibrosis become more apparent. Findings that are suggestive of fibrosis and better visualized on CT scans include traction bronchiectasis, lobular distortion, intralobular lines, and in advanced cases, cystic lung destruction (also called honeycombing). ARDS therapies can also alter the CT scan appearance. The use of perflubron in partial liquid ventilation causes a gravity-dependent patchy or homogeneously white appearance on CT scans. The movement of perflubron out of the lungs has been documented and may occur because of hematogenous spread. Extrapulmonary perflubron may also be present in the lymph nodes, pleural space, mediastinum, and retroperitoneum. CT scanning has also been used to evaluate patients who survive ARDS. In one study, 6-10 months after ARDS patients were discharged from the hospital, CT images of their chests revealed more ventral than dorsal pulmonary fibrosis in 87% patients. The extent of the fibrotic changes correlated with the severity of ARDS as well as the duration of mechanical ventilation during which high peak pressures (>30 mm Hg) or high oxygen levels (>70%) were used.

ARDS is usually treated with mechanical ventilation in the intensive care unit (ICU). The possibilities of non-invasive ventilation are limited to the very early period of the disease or to prevention in individuals with atypical pneumonias, lung contusion, or major surgery patients, who are at risk of developing ARDS. Protective lung strategy improved mortality when patients are ventilated with a tidal volume of 6 ml/kg compared to the traditional 12 ml/kg. Low tidal volumes ($V_t$) may cause hypercapnia and atelectasis because of their inherent tendency to increase physiologic shunt. Extra low tidal volume ventilation was the primary independent variable associated with reduced mortality in the NIH-sponsored ARDSnet trial of tidal volume in ARDS. Plateau pressure less than 30 cm $H_2O$ was a secondary goal, and subsequent analyses of the data from the ARDSnet trial and other experimental data demonstrate that there appears to be no safe upper limit to plateau pressure; regardless of plateau pressure, patients fare better with low tidal volumes. Since ARDS is an extremely serious condition which requires invasive forms of therapy it is not without risk. Mechanical ventilation is an essential part of the treatment of ARDS. However, mechanical ventilation may worsen ARDS. Aside from the infectious complications arising from invasive ventilation with tracheal intubation, positive-pressure ventilation directly alters lung mechanics during ARDS. When these techniques are used the result is higher mortality through barotrauma. This form of stress is thought to be applied by the transpulmonary pressure gradient ($P_l$) generated by the ventilator or, better, its cyclical variations. The better outcome obtained in patients ventilated with lower $V_t$ may be interpreted as a beneficial effect of the lower $P_l$. The way $P_l$ is applied on alveolar surface determines the shear stress to which lung units are exposed. ARDS is characterized by a usually inhomogeneous reduction of the airspace, and thus by a tendency towards higher $P_l$ at the same $V_t$, and towards higher stress on less diseased units. The inhomogeneity of alveoli at different stages of disease is further increased by the gravitational gradient to which they are exposed and the different perfusion pressures at which blood flows through them. The different mechanical properties of alveoli in ARDS may be interpreted as having varying time constants–the product of alveolar compliance× resistance. Mechanical ventilation can exacerbate the inflammatory response in patients with ARDS by including cyclic tidal alveolar hyperinflation and/or recruiting/derecruiting. Alveolar hyperinflation in patients with focal ARDS ventilated with the ARDSnet protocol is attenuated by a physiologic approach to PEEP setting based on the stress index measurement. While the contribution of ventilator-induced lung injury (VILI) to ARDS has not been fully elucidated, it is clear from animal models that mechanical ventilation can cause pathologic changes consistent with ARDS in the absence of other insults. Mechanisms of VILI include alveolar overdistension (volutrauma), repetitive alveolar opening and closure (atelectrauma), oxygen toxicity, and biotrauma, the pulmonary and systemic response to alveolar overdistension that may exacerbate lung inflammation and contribute to multiple organ dysfunction. Efforts to minimize VILI are focused on the use of low tidal volume ventilation to prevent volutrauma, the use of positive end-expiratory pressure (PEEP) to reduce alveolar collapse, and minimization of exposure to potentially harmful oxygen concentrations. Higher levels of positive end-expiratory pressure (PEEP) with or without recruitment maneuvers are often used to improve oxygenation. Using a transient increase in transpulmonary pressure, recruitment maneuvers attempt to open previously atelectatic alveoli. This increase in the size of the ARDS baby lung allows distribution of inspired gas among greater numbers of lung units, leading to less over-distension of individual alveoli and potentially less VILI. Several methods have been described, the most commonly used of which is a sustained inflation breath; for example, 40 cm H₂O for 40 seconds. Another maneuver that appears to be gaining popularity is a step-wise increase in PEEP accompanied by low levels of pressure control ventilation. Common complications of any recruitment maneuver include transient hypotension and desaturation, while pneumothorax and other manifestations of barotrauma have been reported and transient alveolar overdistension during the maneuver may paradoxically worsen VILI.

SUMMARY

There remains a need for addition apparatus and methods for treating ARDS, hemoptysis and similar conditions while maintaining ventilation of a patient. Certain embodiments of the present invention are directed to a respiratory apparatus that provides for simultaneous removal of blood and lung expansion. In certain aspects, such a device, the Hemoblocker, can be used for the treatment of hemoptysis or severe exudative lung conditions. Embodiments of the invention include a barrier filter apparatus and multiport connector that allows closed suction system, continuous ventilation, bronchoscopy and control of bleeding source.

Other embodiments of the present invention are directed for selective ventilation of lung lobes, the ARDS tube and associated respiratory apparatus, can provide selective and/or asynchronous ventilation, selective liquid ventilation, of different lung lobes with different lung compliances and gravity dependency zones.

Other specific properties for local anesthetic coating or channeling the polymer can be applicable for the ARDS tube of for other endotracheal tubes used in intensive care medicine.

Certain embodiments are directed to a barrier filter apparatus comprising: (a) a multiport connector having (i) an endotracheal tube port and scope port that are align on opposite sides of the connector so that a scope can be inserted in the scope port passed through the connector and into an attached endotracheal tube, (ii) a barrier chamber port positioned substantially perpendicular to the central axis of the lumen form by the endotracheal tube port and the scope port, (iii) a suction port positioned opposite the barrier chamber port, and (iv) a treatment port that is substantially parallel to the to the central axis of the lumen form by the endotracheal tube port and the scope port; and (b) a barrier chamber configured to attached to the barrier chamber port and a ventilator by a ventilator port that is position opposite the barrier chamber port, the barrier chamber having a top and a bottom that form the barrier chamber, the barrier chamber comprising barrier filter positioned filter frame and one side of the barrier chamber. The apparatus can have a barrier filter that is a long rectangular shaped filter that is rolled on a supply reel or pin and positioned within the barrier chamber such that one end is connected to key or receiving reel or pin and a portion of the filter is positioned across the chamber such that air flows across the exposed portion of the filter during ventilation.

Other embodiments are directed to a protective catheter comprising: (a) an elongated tubular body having a first end and a second end, and forming a first lumen configured to receive a bronchoscope and a second lumen configured to be connected to a suction device, wherein the first end is configured to be attached to a ventilator and the second is configured to be inserted in an access tube positioned in a patient; (b) a defection tab that partially covers the catheter lumen to deflect airflow; and (c) a suction lumen extends beyond the deflection and provide suction at an offset from the catheter lumen. In certain aspects, the catheter lumen is configured to receive a bronchoscope or other visualization device.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

Still other embodiments are directed to an intubation system comprising: (a) at least one ventilator connected to at least one barrier filter apparatus; (b) an endotracheal tube described herein connected to the endotracheal tube ports of the barrier filter apparatus; and (c) a ventilator control system that can be programmed to control the ventilation through a ventilation lumen and at least one lower bronchial tubes that can be inserted into the lung through the endotracheal tube of (b). In certain aspects, lower bronchial tubes are connected one ventilator and the primary ventilation tube is connected to a separate ventilator, wherein each ventilator can be independently controlled.

Embodiments of the invention are directed to an endotracheal tube comprising: an elongated body having a distal end that is configured for insertion into the lungs. The elongated body forms three lumens, (i) a first lumen for ventilation, (ii) a second lumen for a first lower lobe intubation portion or device, and (iii) a third lumen for a second lower lobe intubation portion or device. The distal portion of the elongated body can be bifurcated directing the distal end of the first lower lobe intubation portion to one lobe of the lung (e.g., left lobe) and directing the distal end of the second first lower lobe intubation portion to a second lobe of the lung (e.g., right lobe). The distal end of the first and second lower lobe intubation portion forms a port providing access the lung lobe into which the portion is positioned. The first lumen can be configured to open into the trachea prior to the bifurcation. The endotracheal tube can have a tracheal cuff that can be expanded to seal against the trachea. The tracheal cuff can be position between, in some instances about midway between the proximal end of the tube and the bifurcation or the tracheal opening of the ventilation lumen. The proximal end of the endotracheal tube can have (i) a ventilation port providing access to the first lumen, (ii) a first lower bronchial tube port providing access to the second lumen, and (iii) a second lower bronchial tube port providing access to the third lumen. The endotracheal tube can be expandable. The endotracheal tracheal tube can be deployed in a contracted form and expanded once deployed in the trachea. In certain aspects the endotracheal tube is configured to expand by telescopic expansion of the contracted state.

In certain aspects an endotracheal tube can comprise an elongated body tapering from a proximal upper tracheal tube portion to a distal lower bronchial tube portion. The lower bronchial tube is configured to be position in one lobe of the lung. The elongated body forms two lumens, a first lumen for access from a proximal port through or traversing the lower bronchial tube portion to a distal opening. A second lumen can be formed that traverses the upper tracheal portion with an opening at about the juncture of the upper tracheal portion to the lower bronchial portion. A second lower bronchial tube can be positioned in the upper tracheal lumen, the second lower bronchial tube extending from the upper tracheal lumen to a lower bronchial portion of the lung, the second lumen or tracheal portion lumen providing access for a lower lobe intubation device to be inserted in the other lobe of the lung. In certain aspects the second lower lobe intubation device is independently insertable relative to the endotracheal tube. The endotracheal tube can comprise a tracheal cuff around the tracheal portion of the tube that can be expanded to seal against the trachea. In certain aspects the tracheal cuff is position in the distal third of the tracheal portion of the endotracheal tube. In other aspects the lower bronchial tube can comprise a bronchial cuff that can be expanded to seal a bronchus. The proximal end of the endotracheal tube has a first lower bronchial tube portion port (port in communication with the lumen that runs from the proximal end to the distal end of the lower bronchial tube portion) and a second proximal access port that is in communication with tracheal tube portion lumen that runs the length of the tracheal tube portion, the tracheal tube portion lumen opening distally in the trachea. In certain embodiments the distal tracheal tube opening is distal with respect to a tracheal cuff. The endotracheal tube can have the lower bronchial tube portion configured to access the right or left lower lobe of the lung.

Other aspects of the invention are directed to a barrier filter apparatus comprising: (a) a multiport connector having (i) an endotracheal tube port and scope port that are align on opposite sides of the connector so that a scope can be inserted in the scope port passed through the connector and into an attached endotracheal tube, (ii) a barrier chamber port positioned substantially perpendicular to the central axis of the lumen form by the endotracheal tube port and the scope port, (iii) a suction port positioned opposite the barrier chamber port, and (iv) a treatment port that is substantially parallel to the to the central axis of the lumen form by the endotracheal tube port and the scope port; and (b) a barrier chamber configured to attached to the barrier chamber port and a ventilator by a ventilator port that is position opposite the barrier chamber port, the barrier chamber having a top and a bottom that form the barrier chamber, the barrier chamber comprising barrier filter positioned filter frame and one side of the barrier chamber. The apparatus can have a barrier filter that is a long rectangular shaped filter that is rolled on a supply reel or pin and positioned within the barrier chamber such that one end is connected to key or receiving reel or pin and a portion of the filter is positioned across the chamber such that air flows across the exposed portion of the filter during ventilation.

Other aspects include a protective catheter comprising: (a) an elongated tubular body having a first end and a second end, and forming a first lumen configured to receive a bronchoscope and a second lumen configured to be connected to a suction device, wherein the first end is configured to be attached to a ventilator and the second is configured to be inserted in an access tube positioned in a patient; (b) a deflection tab that partially covers the catheter lumen to deflect airflow; and (c) a suction lumen extends beyond the deflection and provide suction at an offset from the catheter lumen. In certain aspects the catheter lumen is configured to receive a bronchoscope or other visualization device. In other aspects the catheter comprises a lumen configured to be connected to a suction device and a camera position at the distal end of the catheter. The camera is coupled to a visualization device at the proximal end of the catheter or outside of the subject in which the catheter is to be deployed.

Still other embodiments are directed to an intubation system comprising: (a) at least one ventilator connected to at least one barrier filter apparatus; (b) an endotracheal tube described herein connected to the endotracheal tube ports of the barrier filter apparatus; and (c) a ventilator control system that can be programmed to control the ventilation through a ventilation lumen and at least one lower bronchial tubes that can be inserted into the lung through the endotracheal tube of (b). In certain aspects lower bronchial tubes are connected one ventilator and the primary ventilation tube is connected to a separate ventilator, wherein each ventilator can be independently controlled.

In certain aspects of the embodiments described herein all the connectors, valves, sensors, ventilator, and ventilator controls can be configured, programmed, and/or monitored for asynchronous ventilation.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIGS. 19A-B. (A) illustration of initial insertion with collapsed cuff (B) Illustrates lobe isolation configuration with inserted secondary tubes.

FIG. 20. Dimensional diagram of the backwards compatible tracheal tube.

FIG. 25. Closeup on Cuff

FIG. 26. Inside View of Cuff

FIGS. 27A-B. (A) Right Secondary Tube. (B) Left Secondary Tube.

DESCRIPTION

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

I. BARRIER FILTER

Figure 1:
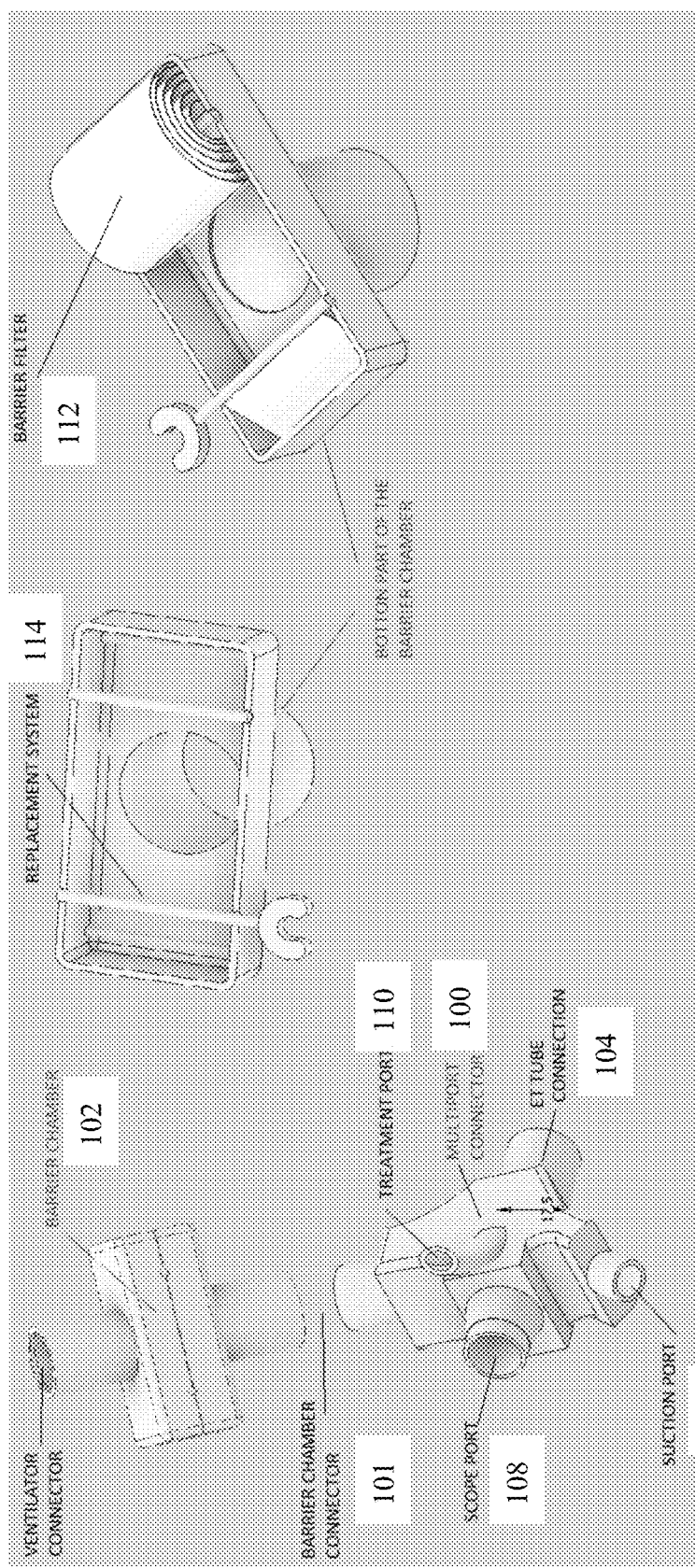
FIG. 1. Illustration of one embodiment of a barrier filter apparatus.

One embodiment is a close suction system with a barrier filter apparatus for managing massive hemoptysis and pulmonary edema. The barrier filter apparatus can be connected to a ventilator and an endotracheal tube and positioned outside of a patient. FIG. 1 illustrates one embodiment of a barrier filter apparatus. The apparatus comprises multiport connector 100 and barrier chamber 102. Multiport connector 100 can be connected with barrier chamber 102 through barrier chamber port 101. Mulitport connector 100 can also be connected with an endotracheal tube using endotracheal tube (ETT) connector 104. Multiport connector 100 can have three additional ports, suction port 106, fiber optic scope port 108, and therapy port 110 for insertion of bronchial blocker or drug administration (aerosol or nebulizer). All the ports have unidirectional and air seal valves that allow continuous ventilation. The position of each port is strategically designed according to purpose or function. Suction port 106 is located so that all the bleeding from the airway will flow by gravity and drain to a the valve where the suction catheter is located, and allowing free airflow from the apparatus to the ventilator.

Barrier chamber 102 chamber comprises barrier filter 112 that blocks or traps blood and prevents it from reaching the limbs of the respiratory circuit. Barrier filter 112 allows free airflow and does not significantly interfere with ventilation. Barrier filter 112 is located inside barrier chamber 102. The filter has a replacement system 114 that allows placement of a new and clean barrier without disconnection or interruption of ventilation in case the blood reaches the filter. In certain aspects, a portion of barrier filter 112 is position across the port so that that portion of the barrier filter is exposed to air flowing perpendicular to the plane of the portion of the barrier filter so positioned. The exposed portion of the barrier filter can be replaced by moving the barrier filter laterally so that a new unexposed portion of the barrier filter is positioned across the port. In certain aspect the barrier filter is provided in a roll that can be unrolled without opening barrier chamber 102. In a further aspect the exposed portion of the barrier filter can be rolled and stored in the barrier chamber without opening barrier chamber 102.

The barrier filter apparatus provides for continuous ventilation, a close suction system, and a barrier filter. The device prevents ETT disconnection, prevents blood from reaching the limbs of the respiratory system, allows suctioning of the blood, and allows the use of PEEP (higher gas flows may be necessary). If the blood reaches or saturates the exposed barrier filter, it can be easily and quickly exchanged by a new portion of filter preventing contamination of the respiratory circuit or a capnograph line.

II. ACUTE RESPIRATORY DISTRESS SYNDROME (ARDS) TUBE

Figure 2:
FIG. 2. Computed tomography scan in a patient with acute respiratory distress syndrome.

Another embodiment of the invention is a tracheal-bronchial tube or an acute respiratory distress syndrome tube (ARDS tube). The ARDS TUBE is a respiratory apparatus specifically designed for mechanical ventilation of patients suffering from acute respiratory distress syndrome (ARDS) and similar lung pathologies. ARDS is a severe medical condition characterized by diffuse inflammation of the lungs, causing infiltrates predominantly in the gravity dependent areas. The infiltrated zones will have lower compliance requiring higher pressures to expand and remain open when compared with the zones with no infiltrates. If the entire lung is ventilated with higher pressures, the well aerated zones with no infiltrates will hyper inflate and over distend, causing ventilator induced lung injury (VILI). Improvements on the imaging aspects of ARDS, particularly CT Scan, show that diseased lungs have a very heterogeneous pathology. In about 14% of cases the infiltrates are diffuse and in 86% of the cases the lung infiltrates are located in gravity dependent areas. For patients in supine position, the gravity dependent areas will be located into the postero-basal segments (see for example FIG. 2). Most of the postero-basal regions of the lungs belong to the inferior lobes of the right and left lungs.

Figure 3:
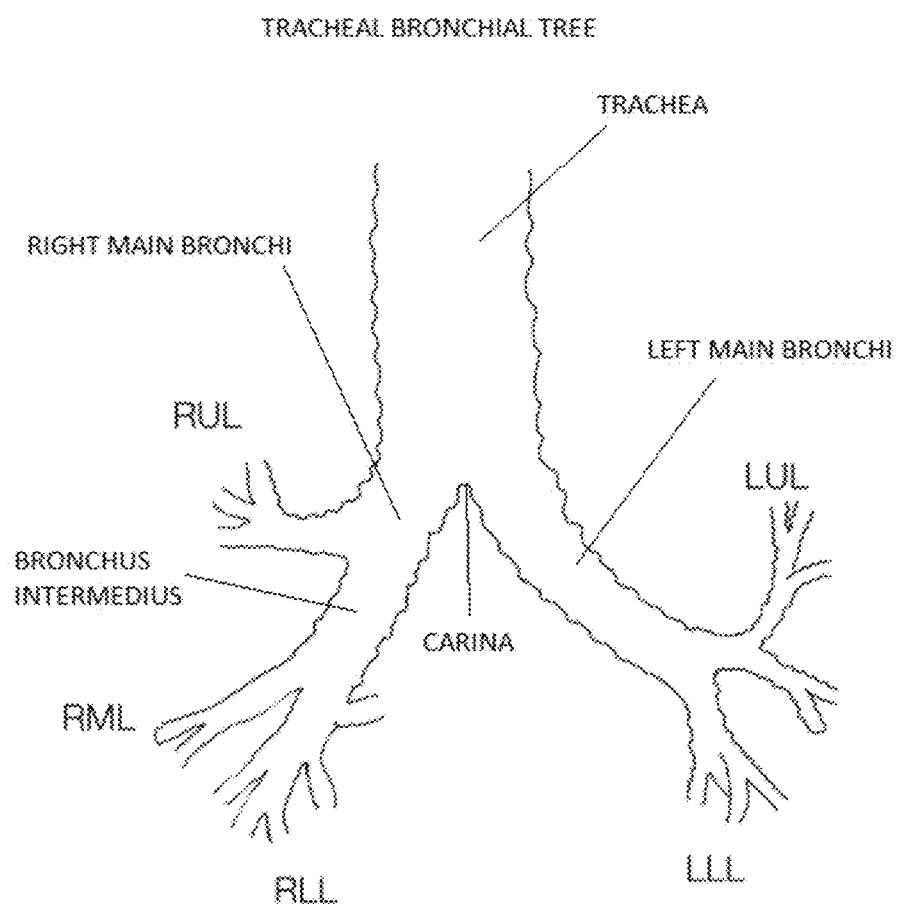
FIG. 3. Illustration of a tracheal bronchial tree. RUL—right upper lobe, RML—right middle lobe, RLL—right lower lobe, LUL—left upper lobe, LLL—left lower lobe.
Figure 4A:
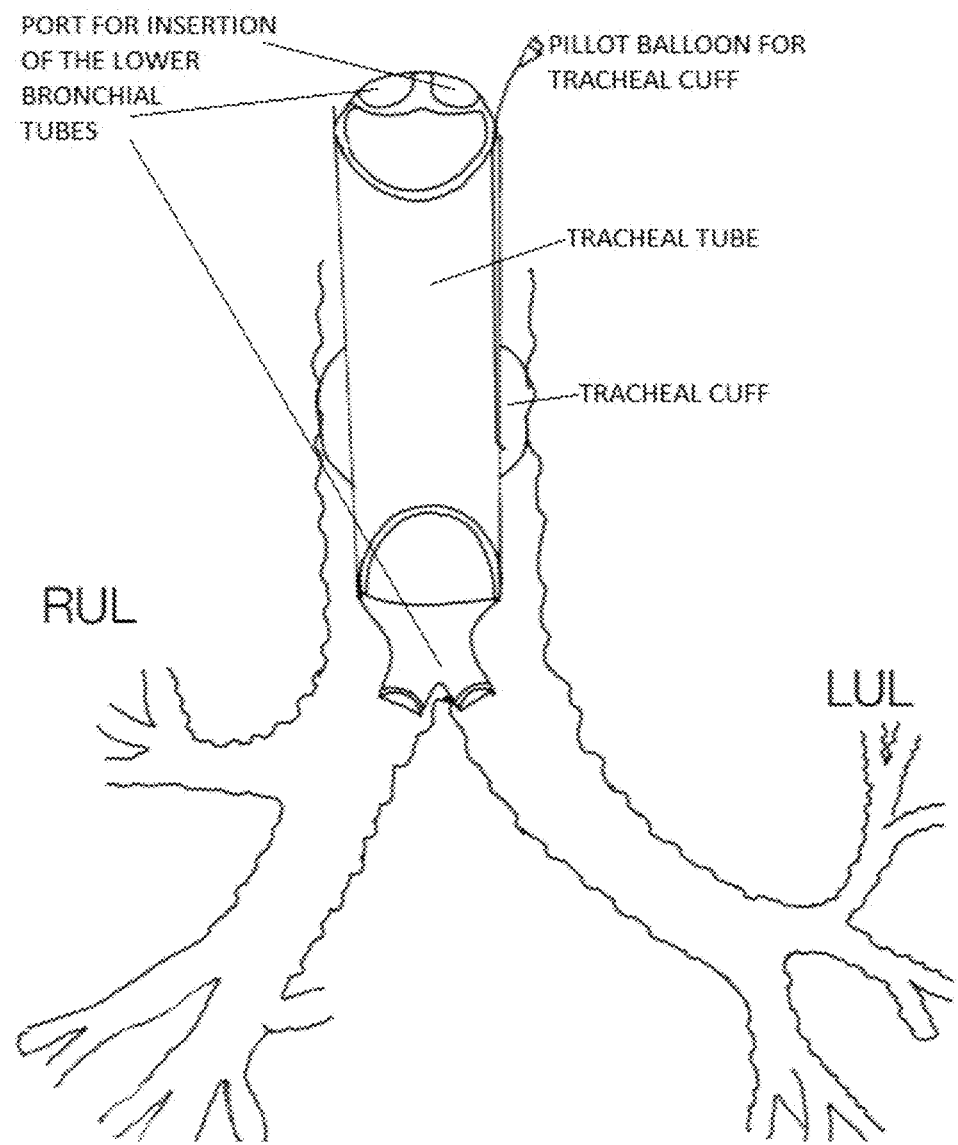
FIGS. 4A-D. Illustration of one embodiment of an ARDS tube deployed in the lungs. (A) RUL—right upper lobe, RML—right middle lobe, RLL—right lower lobe, LUL—left upper lobe, LLL—left lower lobe.
Figure 4B:
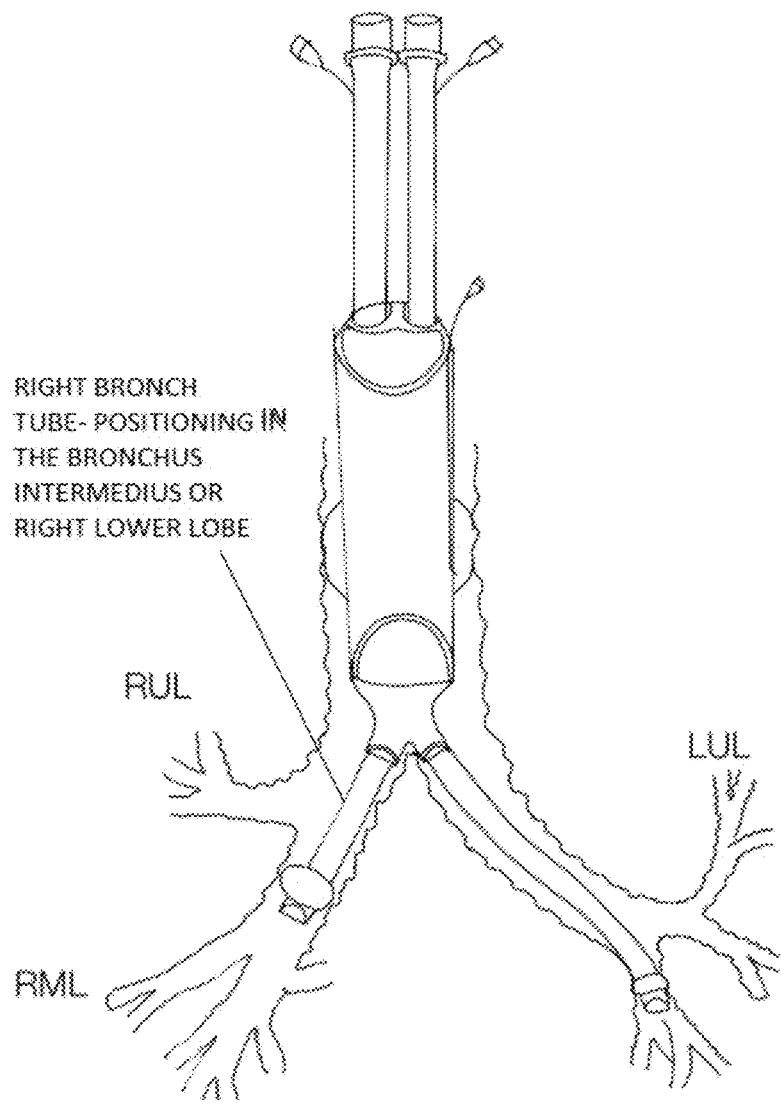
Figure 4C:
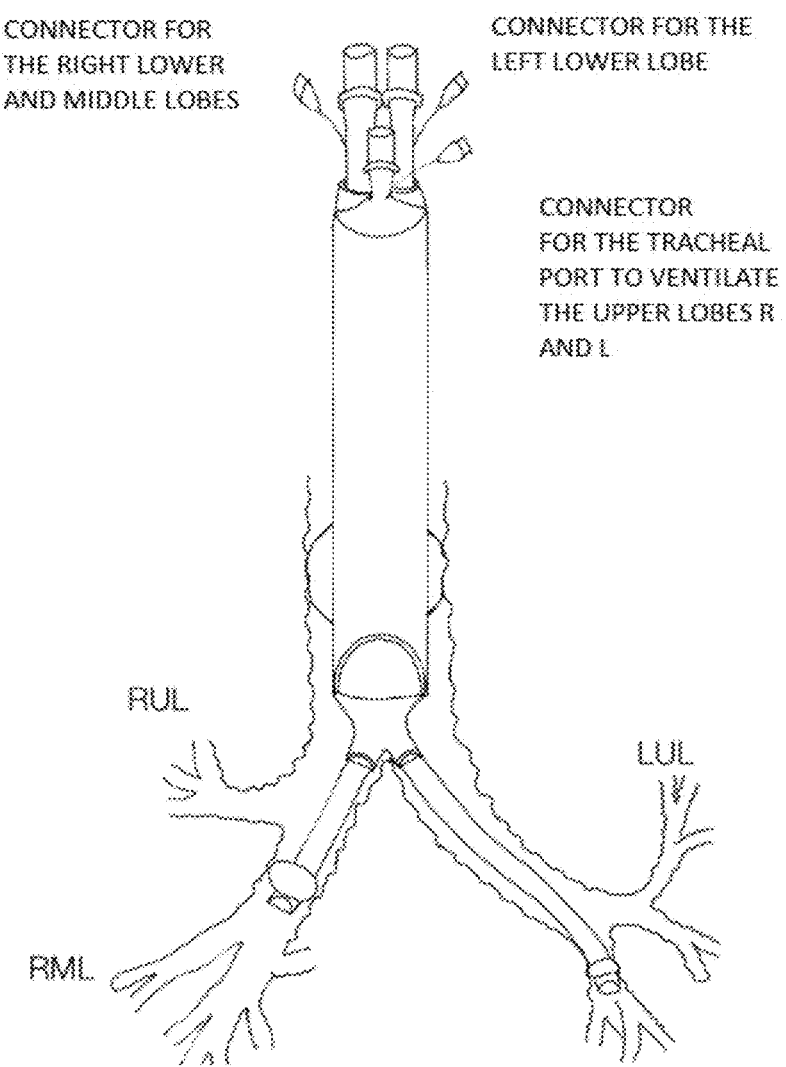
Figure 4D:
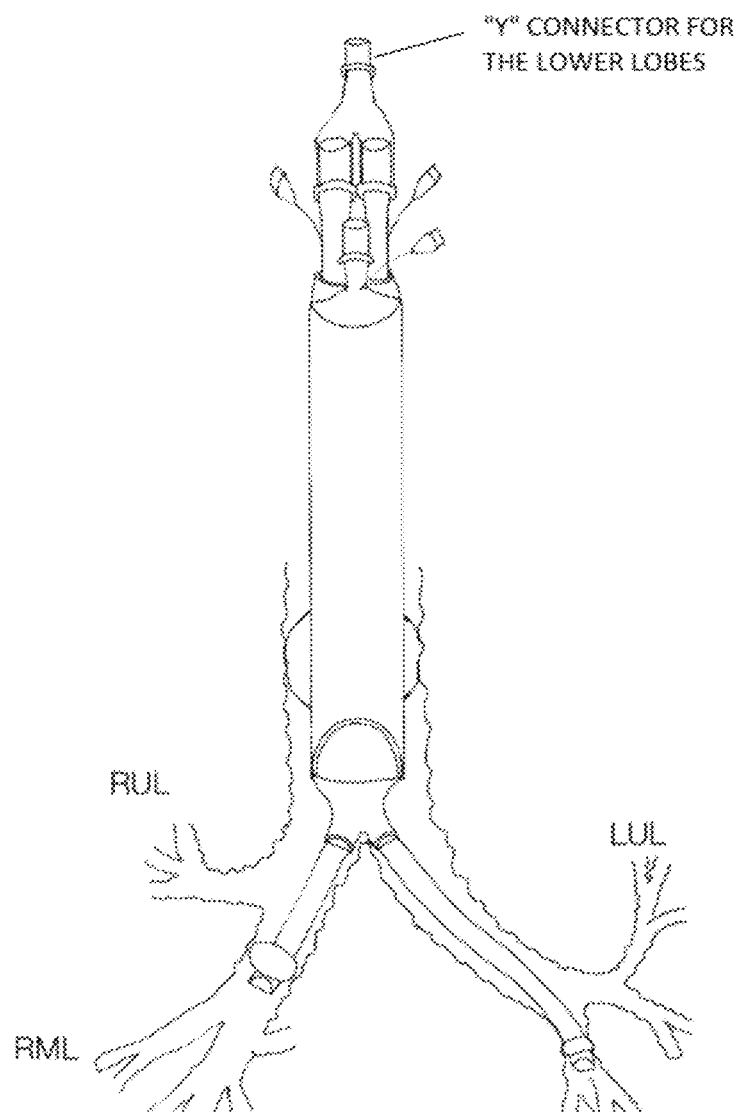
Figure 5A:
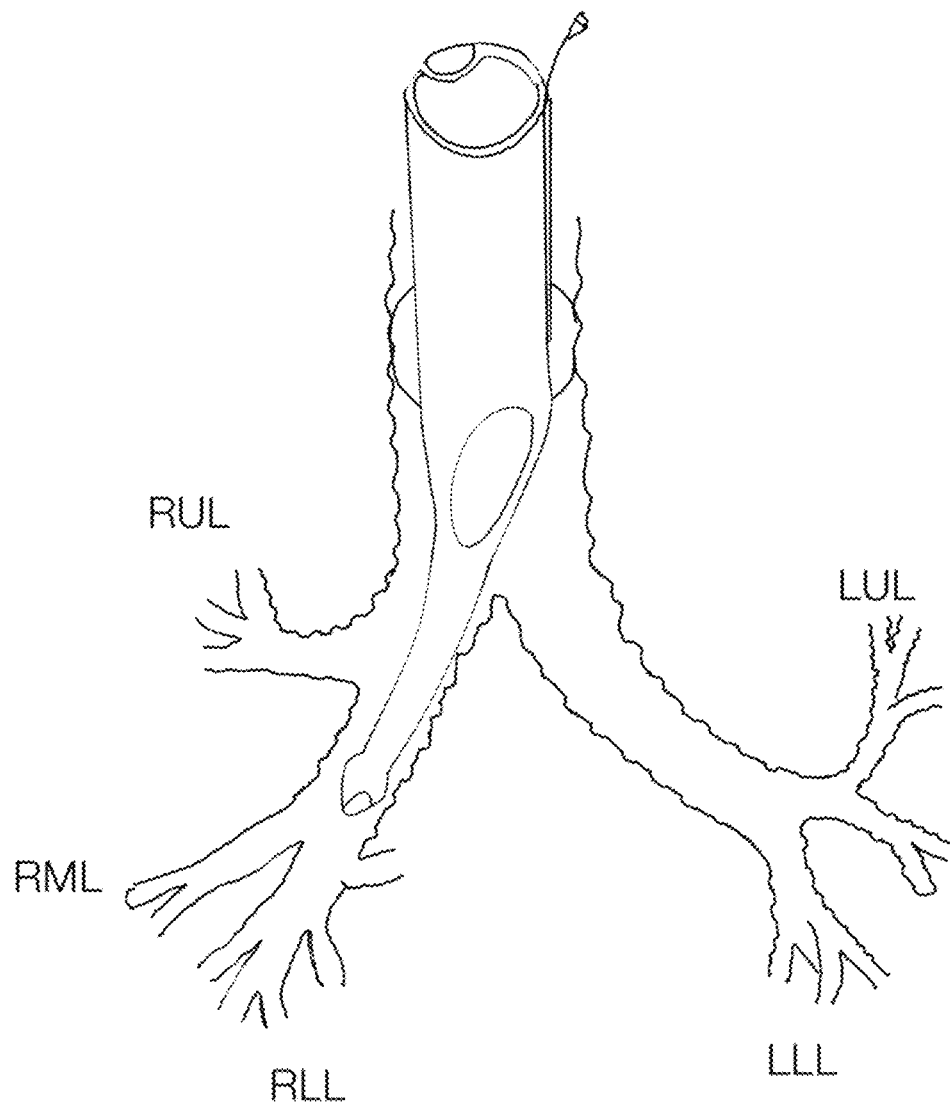
FIGS. 5A-D. Illustration of an alternative embodiment of an ARDS tube deployed in the lungs. RUL—right upper lobe, RML—right middle lobe, RLL—right lower lobe, LUL—left upper lobe, LLL—left lower lobe.
Figure 5B:
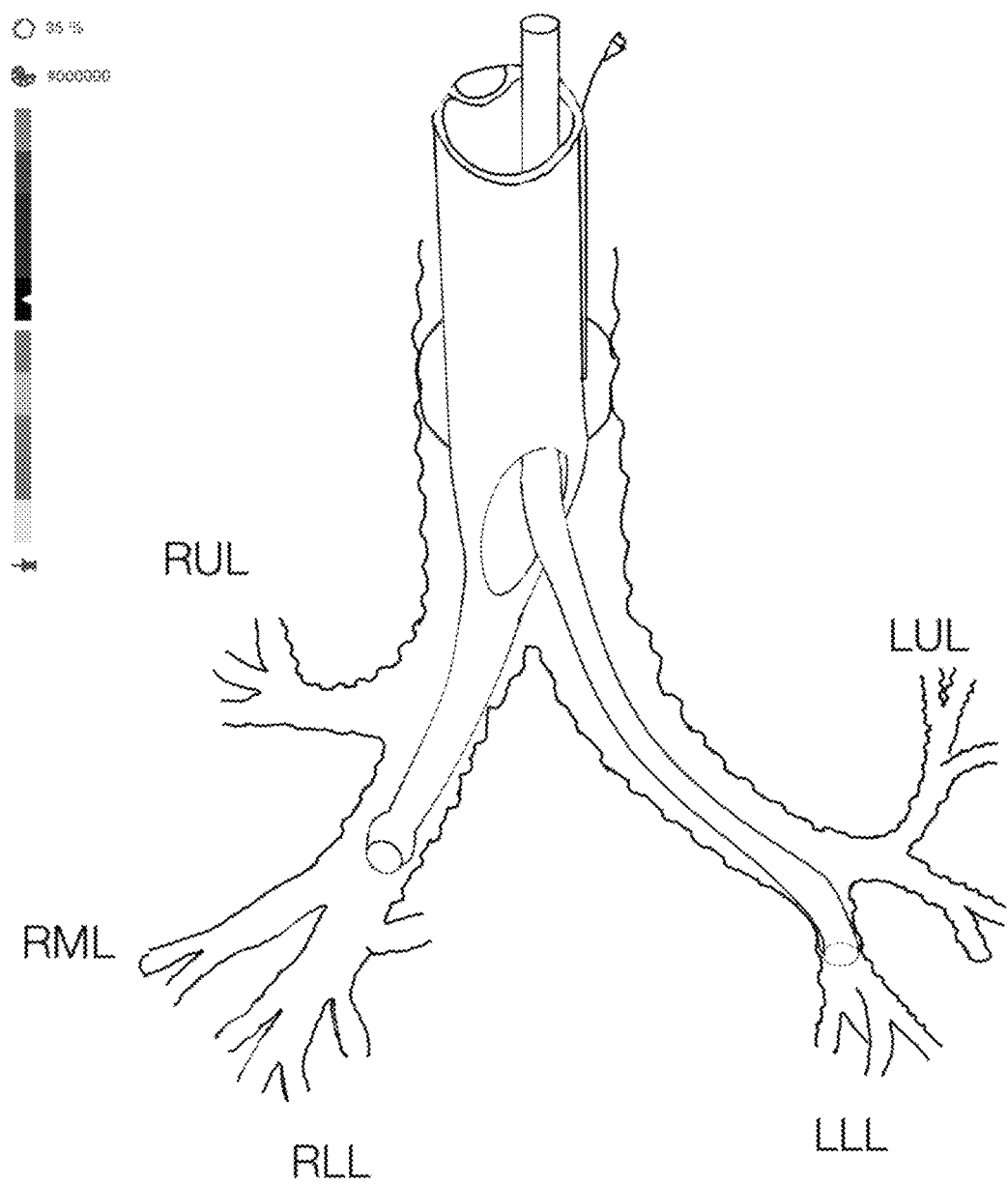
Figure 5C:
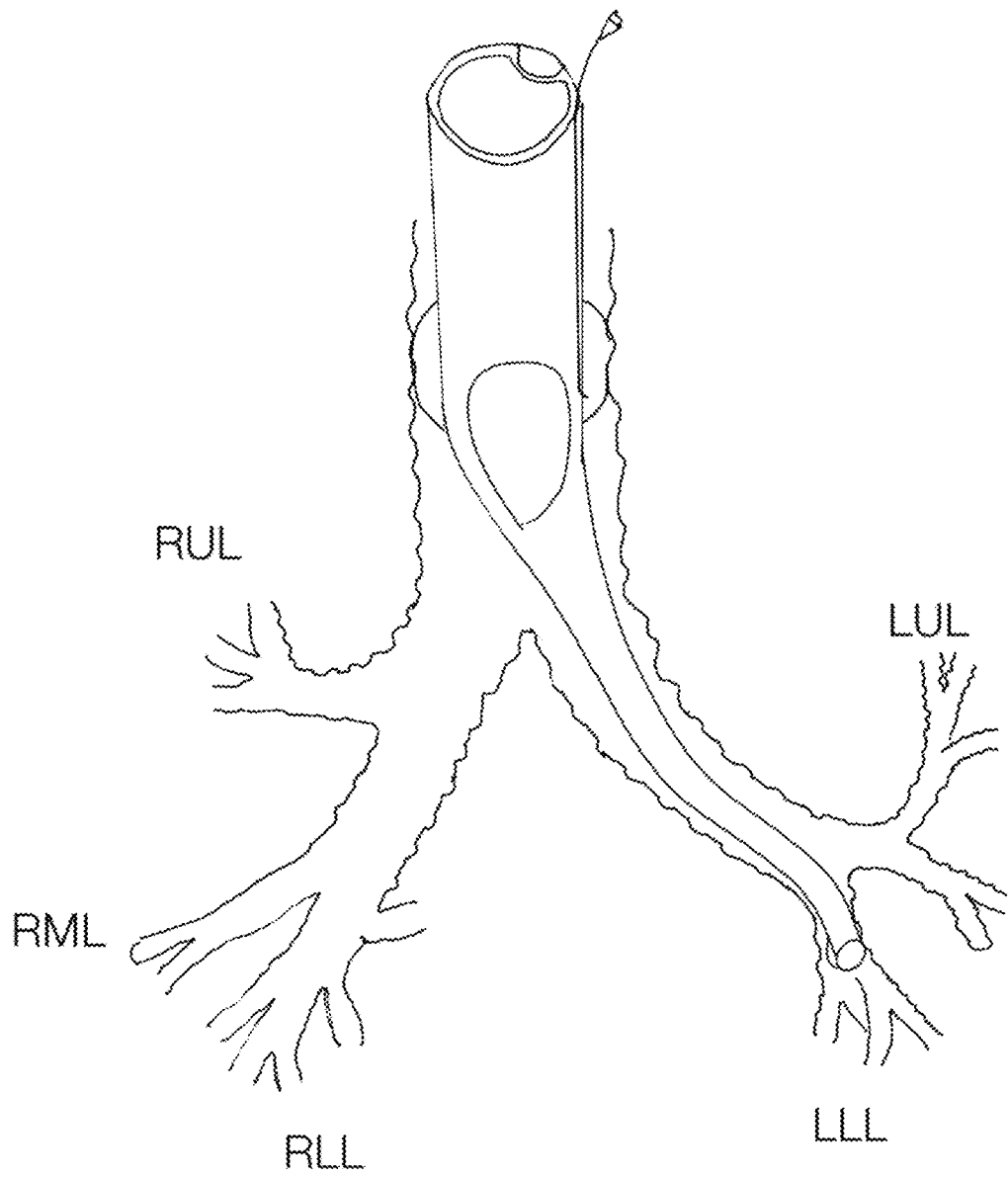
Figure 5D:
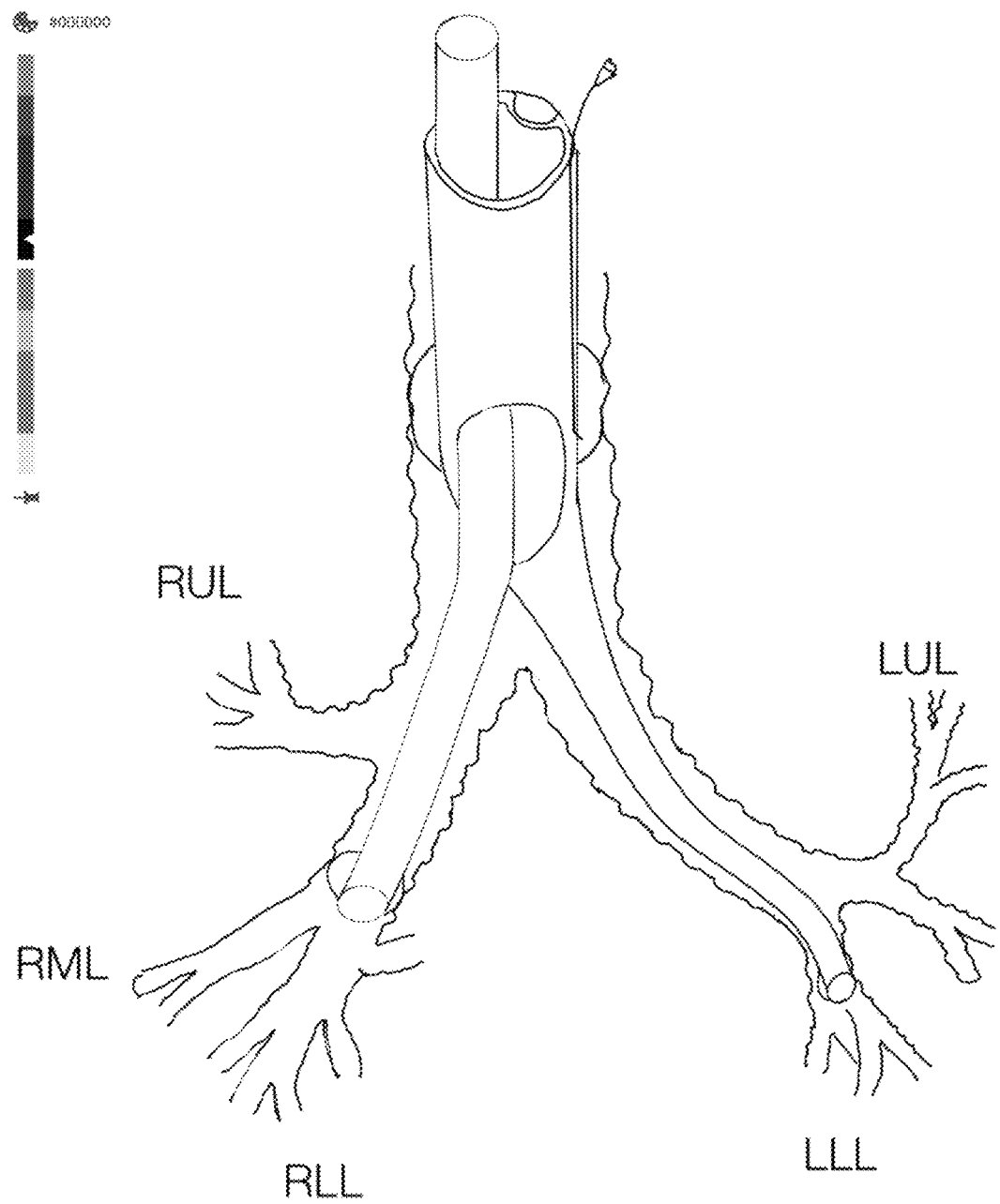
Figure 6:
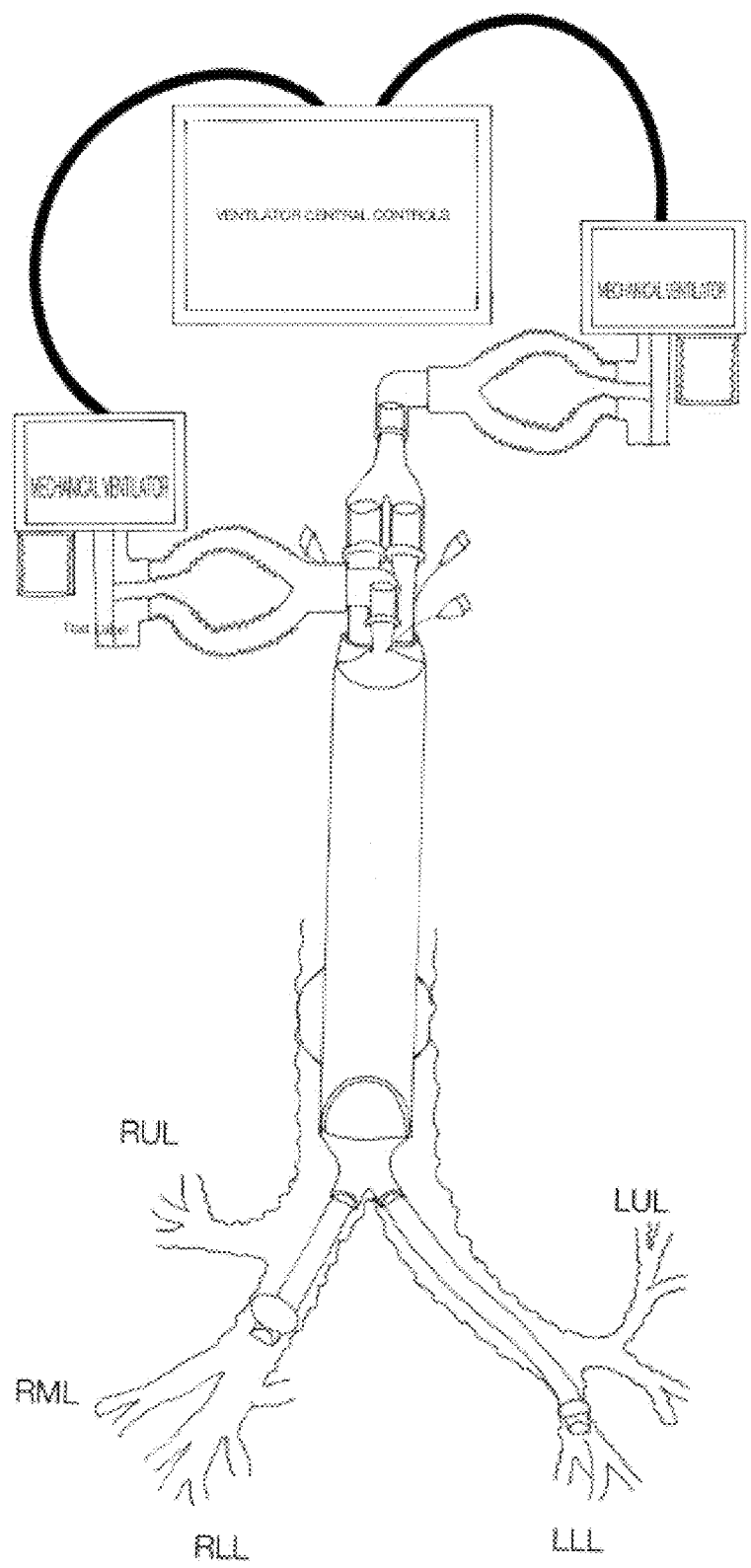
FIG. 6. Illustrate one example of an intubation system.

The ARDS tube is designed to isolate lower lobes of the lungs allowing selective mechanical ventilation and potential pharmacological treatment of the gravity dependent lung zones. The lung mechanics can be divided in two parts, zones of normal compliance and zones of poor compliance. Selective ventilation of the inferior lobes allows use of different ventilation modes and/or settings for lungs regions with different compliances. Gravity dependent zones, can be separated from the rest of the lung with relatively normal compliance (left upper lobe (LUL), right upper lobe (RUL) and middle lobes) (FIG. 3):

1 tube for the right side lower lobe and trachea;
2 is 1+bronchial tube to the left;
3 tube for the left side lower lobe and trachea; and
4 is 3+bronchial tube to the left lower.

The ARDS tube can isolate and thus provide asynchronous ventilation the lower and upper lungs. This feature would allow lower peak pressures since there is more space into the thoracic cavity to ventilate the lobes separately. The lower and upper lungs can be ventilated asynchronous, when the upper inflates the lower deflates and vice versa. Alternatively, the lower and the upper lungs can be ventilated totally synchronic or in partial syncrony where the lower lungs would expand totally before the inflation of the upper lungs. This feature would prevent barotrauma or voluntary a secondary to elevated peal pressures. The other interesting feature is the possible application of differential PEEP.

One embodiment of the invention is directed to an endotracheal tube comprising: (a) an elongated body forming three lumens, a first lumen for ventilation, a second lumen for a first lower lobe intubation device, and a third lumen for a second lower lobe intubation device, wherein the bottom portion is bifurcated directing one port to the left lobe of the lung and directing a second port to the right lobe of the lung, and the first lumen opening into the trachea prior to the bifurcation; (b) a tracheal cuff that can be expanded to seal against the trachea; (c) a ventilation port providing access to the first lumen, a first lower bronchial tube port providing access to the second lumen, and a second lower bronchial tube port providing access to the third lumen. The endotracheal tube can be an expandable endotracheal tracheal tube that can be deployed in a contracted form and expanded once deployed in the trachea.

Another embodiment is directed to an endotracheal tube comprising: (a) an elongated body tapering from a tracheal tube portion to a lower bronchial tube portion that can be position in one lobe of the lung, the body forming two lumens, a first lumen for access through the lower bronchial portion of the tube, and a second lumen terminating in a tracheal tube port that provides access for a lower lobe intubation device to be inserted in the other lobe of the lung; (b) a tracheal cuff around the tracheal portion of the tube that can be expanded to seal against the trachea; (c) a first lower bronchial tube portion port and a second access port in communication with tracheal tube portion lumen at the top of the tube. The endotracheal tube can have the lower bronchial tube portion configured to access the right or left lower lobe of the lung The bronchial tubes for ventilation of ARDS patients are positioned in the lower bronchus in order to selective provide ventilation for the lower lobes. The left lower lobe branch is usually long enough and to position the bronchial tube and have a small cuff inflated. The right lower lobe bronchus is usually very short; in this case the right bronchi tube cannot be positioned in the *bronchus intermedius*.

The ARDS tube can also be used for lung isolation often needed in thoracic surgery. The bronchi tube can be alternatively positioned in the main stem bronchi and that will provide selective ventilation to the desired lung. It is current practice to exchange the double lumen tube at the end of a thoracic surgery. With the use of the ARDS tube the bronchial tubes can be removed and in the end it will work as a regular single lumen tube.

The dimensions of the ARDS tube also can be sized and potentially customized based on the patient's tracheal bronchial tree size. With the CT scan or MRI three-dimensional reconstruction, and conversion from imaging such as files to the 3D rendering format such as stereolithography files, endotracheal bronchial tubes can be designed with the ideal size and shape for an specific patient.

III. BRONCHOSCOPY

Figure 7:
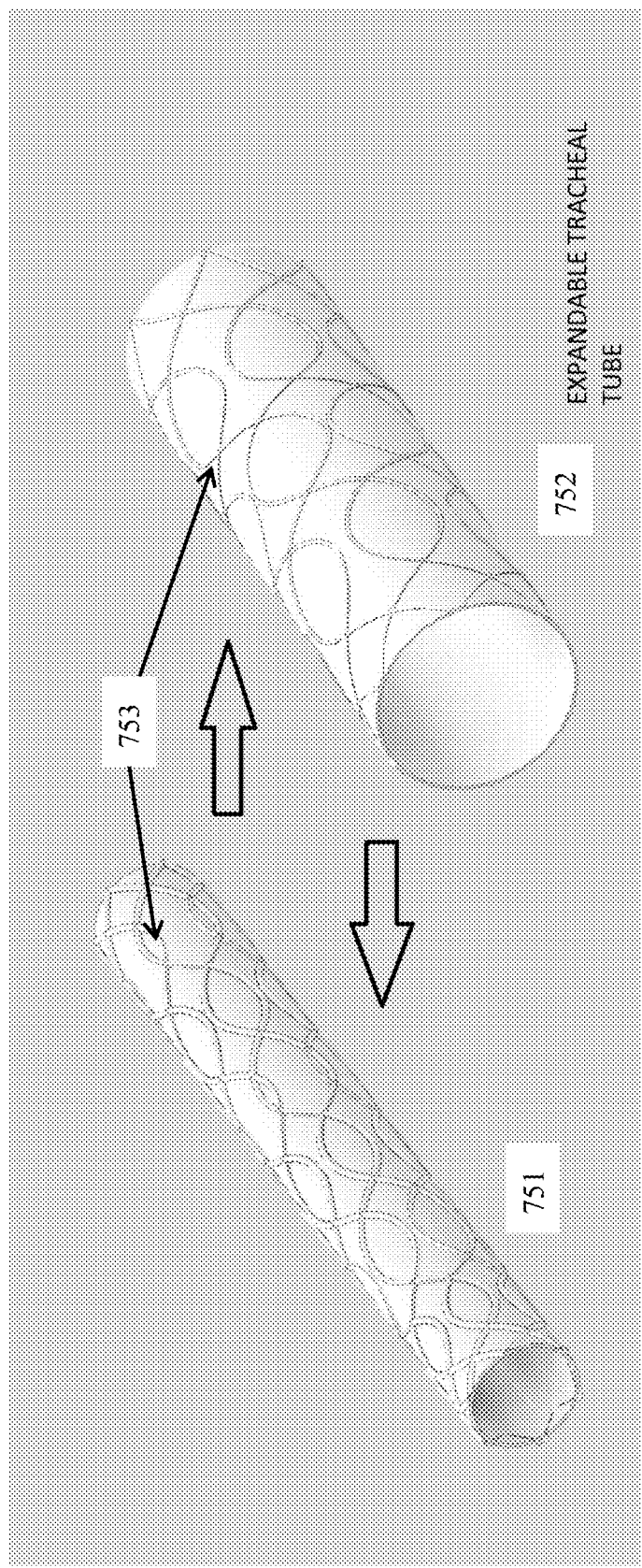
FIG. 7. Illustration of an expandable tracheal tube.
Figure 8A:
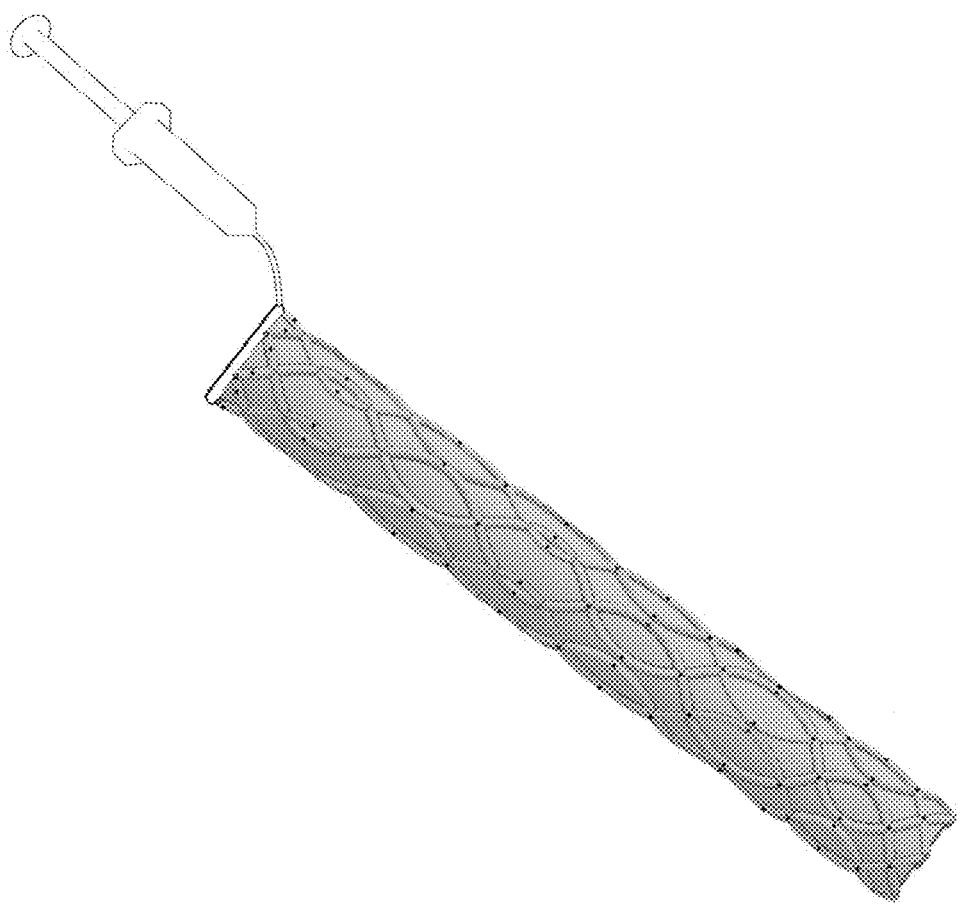
FIGS. 8A-C. Illustrates a drug eluting tracheal tube.
Figure 8B:
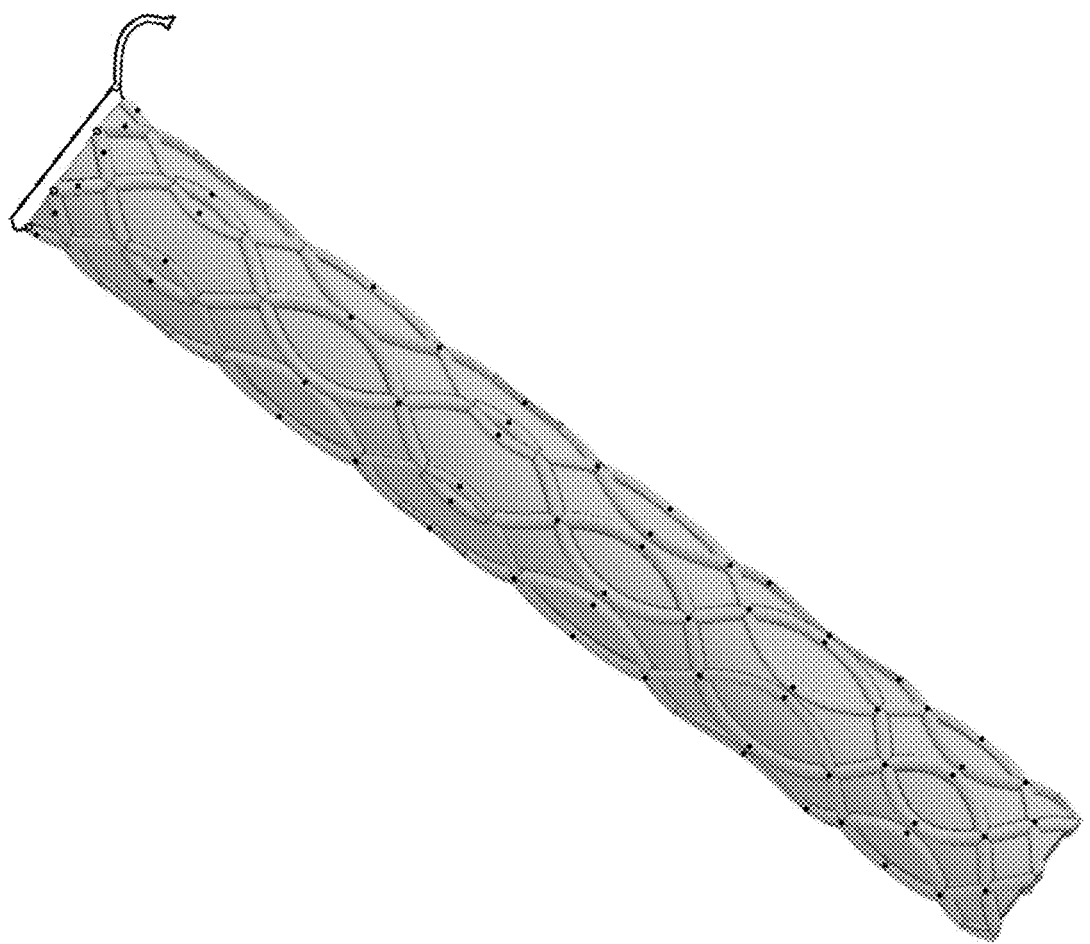
Figure 8C:

Bronchoscopy is the diagnostic method most frequently used to identify, tamponade and treat the source of bleeding in the tracheal bronchial tree. The flexible bronchoscopes, adult or pediatric, have diameter small enough to be introduced inside the endotracheal tube. An important limitation of the endotracheal tube for selective lung or lobe ventilation is the diameter. A large diameter tube is usually needed to accommodate the bronchial tubes. The endotracheal tubes need to be passed through the vocal cords and cricoid subglottic area, which has smaller diameter when compared to the trachea. Certain aspects include an endotracheal tube having a stented mesh (753) embedded in the polymer (FIG. 7). The endotracheal tube can have an initial internal diameter between 35 to 55 mm (illustrated by ET 751 of FIG. 7) and after expansion (illustrated by ET 752 of FIG. 7) it can potentially reach much larger diameters ranging from 80 to 150 mm. The expansion of the tube can be performed by balloon expansion of by a delivery system composed by an external sheath that will maintain the tube with the smaller profile until the time for deployment when the tube will expand once the sheath is removed.

Figure 9A:
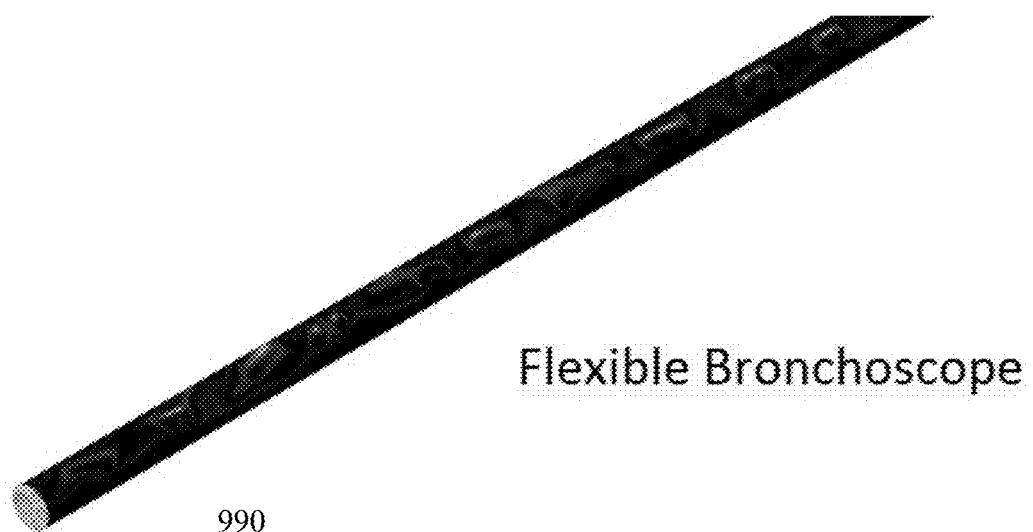
FIGS. 9A-B. Illustrates a flexible bronchoscope.
Figure 9B:
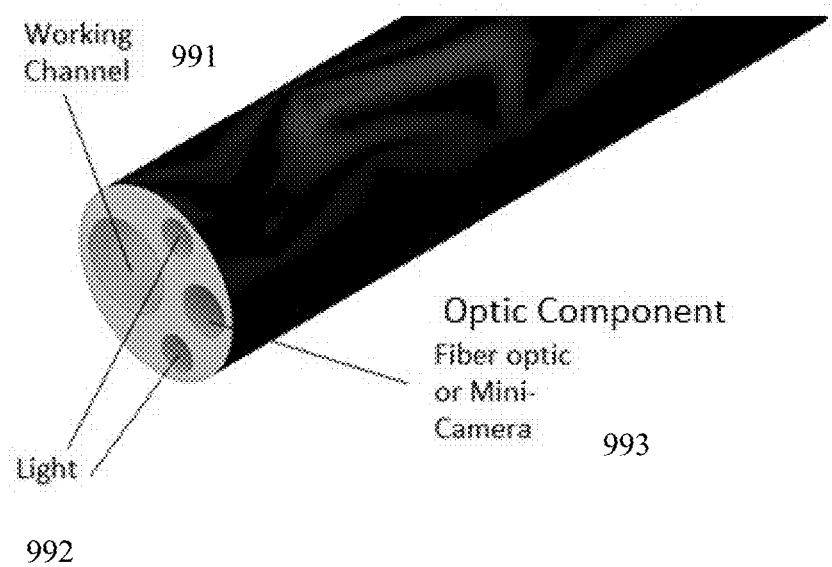
Figure 10A:
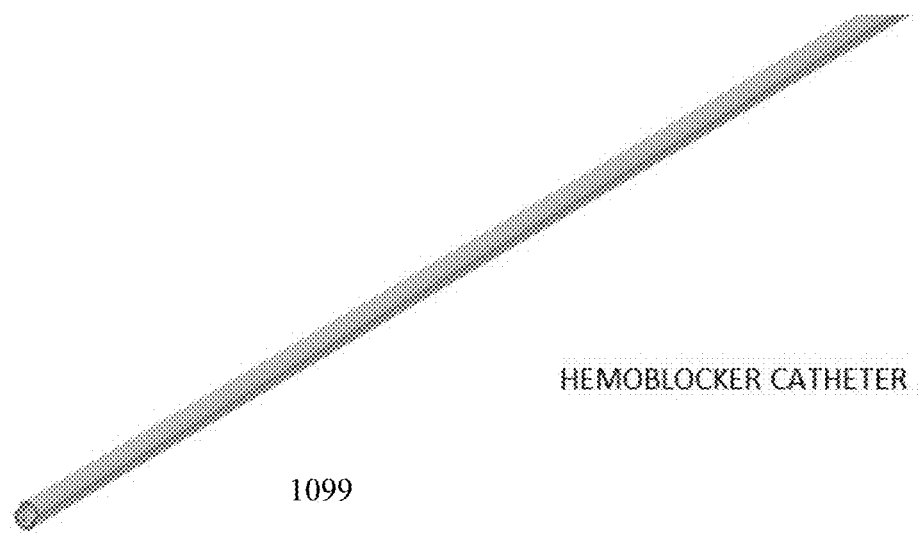
FIGS. 10A-B. Illustrate a hemoblocker catheter.
Figure 10B:
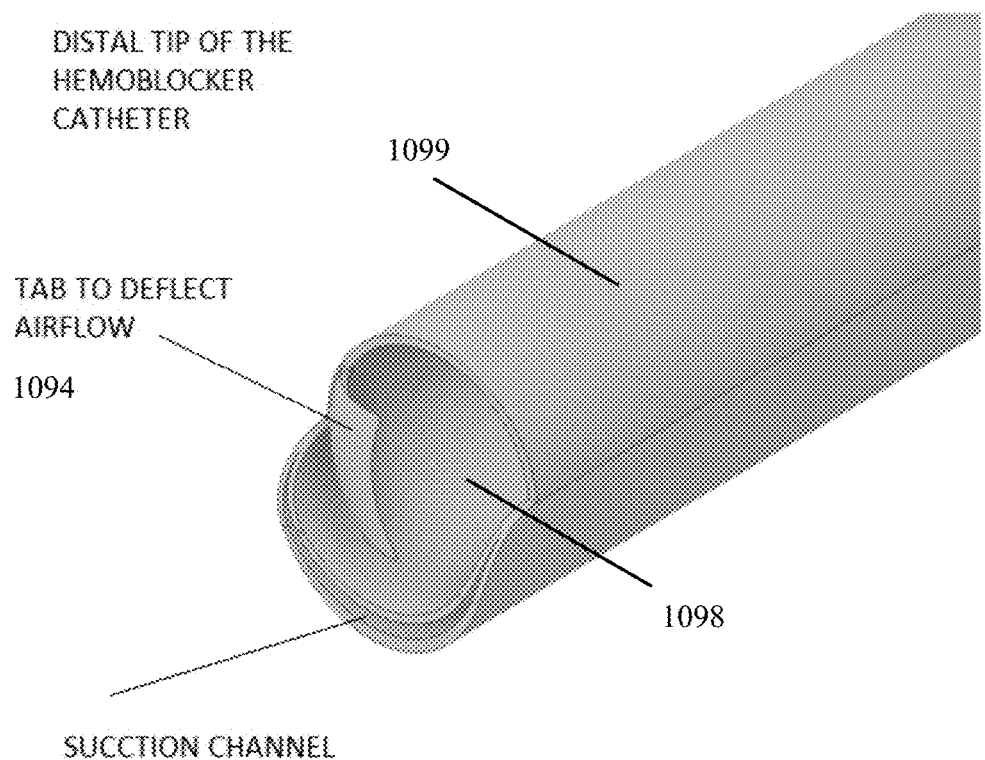
Figure 11A:
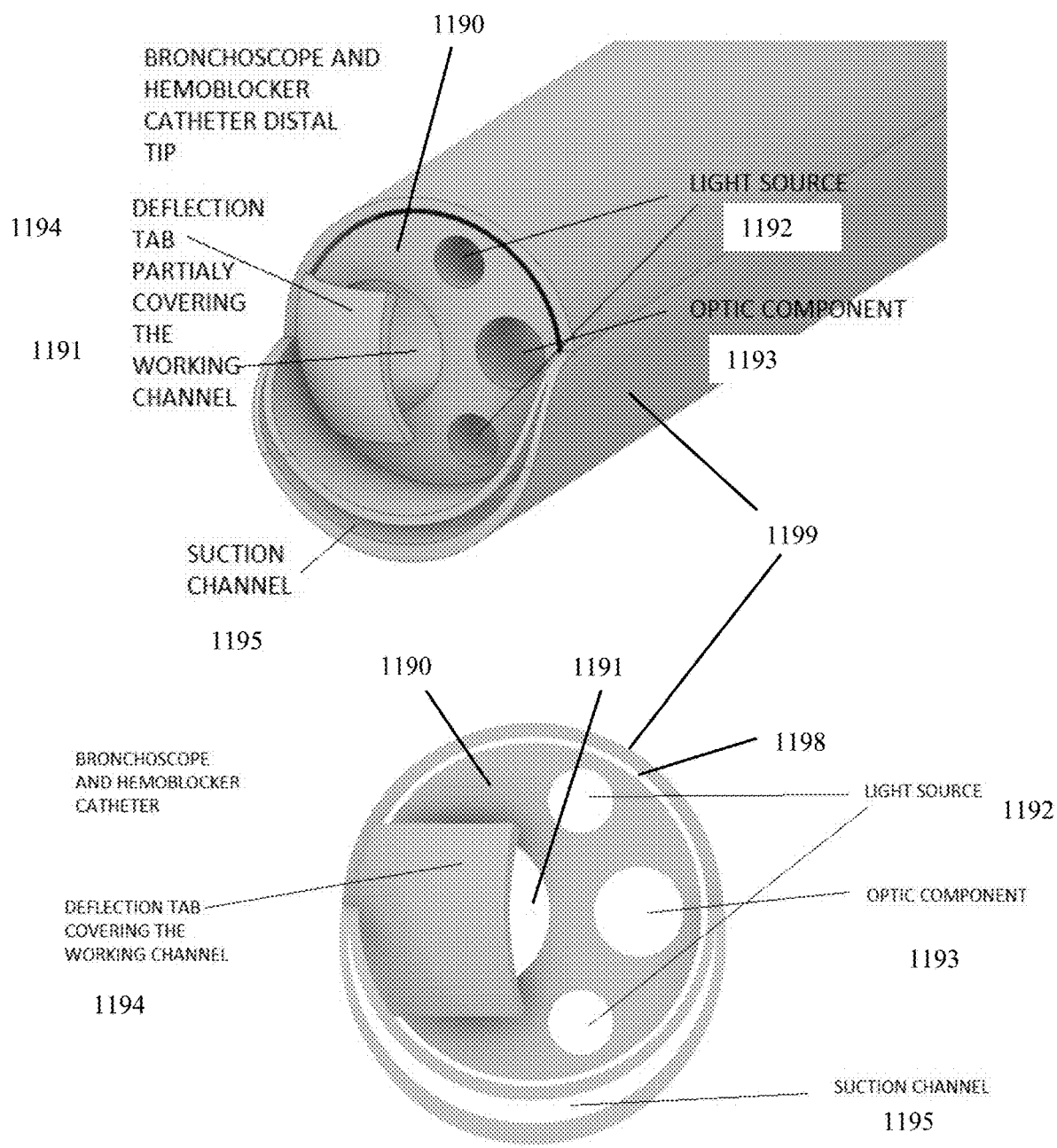
FIGS. 11A-B. Illustrate a hemoblocker catheter with a bronchoscope deployed in the lumen.

The visualization of the inside of the bronchial tree is provided by an optical component that is embodied by a very small optic fiber of mini camera and light source at the tip of the scope (for example see FIG. 9, FIG. 10, or FIG. 11). If blood or secretions touch the lens of optic component (993, 1093, 1193) the visualization is lost. Suction and cleaning of the lens is necessary to continue the procedure and it is normally necessary to remove the scope from the airway to proper clean the lens. Working channel 991, 1091, 1191 of the scope can be used exclusively for suction, irrigation or flow oxygen separately. It is a single lumen small channel that is usually not efficient for vigorous suction.

Figure 11B:
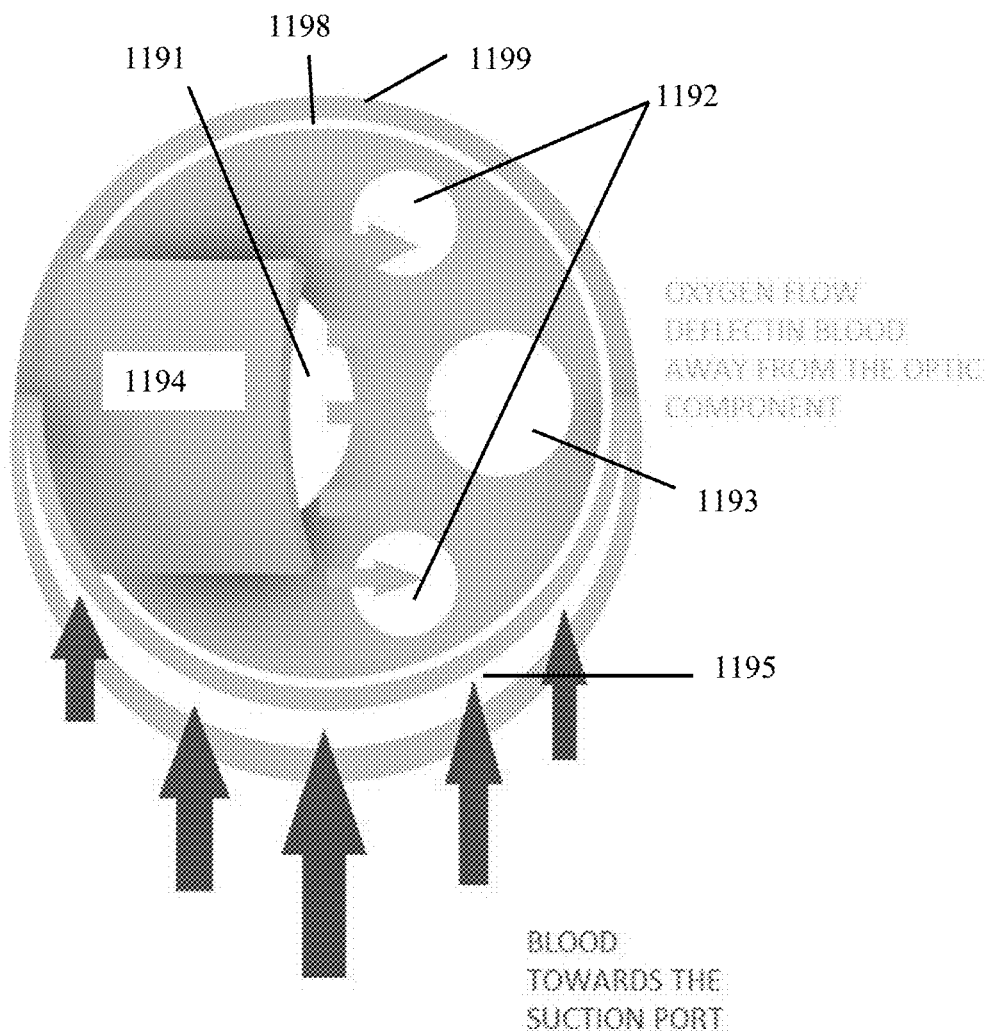

The hemoblocker catheter (1099, 1199) is a double lumen catheter, one lumen for the bronchoscope 1091, 1191 and a second exclusive lumen for suction (1098, 1198). The catheter aims to maintain the lens clean by deflecting the oxygen flow from the working channel and redirecting it towards the lens (FIG. 11B). At the same time the suction channel (1095, 1195) from the hemoblocker catheter is positioned few millimeters ahead of the scope (FIG. 11A) providing a preferential path for the blood or secretions to be suction before they can reach the lens of the optical component. Oxygen needs to be connected to the working channel of the scope (991, 1091, 1191) and suction connected to the suction channel (1095, 1195) of the hemoblocker catheter (1099, 1199).

Critical ill patients or patients that chronically depend of prolonged mechanical ventilation are often required to be sedated due to discomfort caused by the endotracheal tube. The endotracheal tube, by touching the highly innervated mucosa of the mouth, pharynx, larynx and trachea will cause discomfort, cough, gagging, or vomit reflex. However, it is well known in the field of anesthesiology that if local anesthetic is properly applied to the airway, an endotracheal tube can be inserted with mild or no discomfort. Herein it is describing the use of drug eluting polymer with local anesthetic medication and endotracheal tube with microporous channels on the out surface to inject local anesthetic drug allowing refilling of the medication.

Prolonged permanence mechanical ventilation is associated with pneumonia due to multiple factors such as poor clearance of secretions and formation of a biofilm. The biofilm creation can be inhibited by the presence of antibiotic coating or embedded polymer. Herein is describe the use of an endotracheal tube made of polymer embedded and/or coated with antibiotic drugs to prevent bacterial growth.

IV. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Performance Specifications

Materials.

Materials of the product should be IAW ASTM F 1242 section 4.1.1 where materials intended to be inserted into patient shall be nontoxic and compatible with human tissue (14.1). Materials of the product should be IAW Implantation Test, Cell culture test or with ASTM F 813: Practice for Direct Contact Cell Culture Evaluation of Materials for Medical Devices (14.1). The primary and secondary tubing for the product may be reusable if IAW (4.1.2) of ASTM F 1242 where materials must be resistant to deterioration by chemical cleansing agents and sterilization, and autoclaving if using steam sterilization (14.1). The product should also be resistant to anesthetic chemicals. It should also function satisfactorily in the presence of anesthetic agents and gases used. The product and prototype should have sufficient strength to resist deformation under normal use. The primary and secondary tubing must not collapse from cuff inflation. All tubing should be able to pass the ASTM F 1242 Collapse test (14.1). Both the prototype and product must be considered to be kink resistant to prevent collapsing while inserted in the patient's airway. IAW F 1242 ASTM standard specifications, the product should follow the F 640 Test Methods for Radiopacity of Plastics for Medical use (14.1). All tubing shall be transparent to allow visibility with fiber optic endoscopes. Tracheal tubes with tube connectors supplied as "sterile" shall satisfy the requirements of EN 556-1:2001, 4.1 and, if applicable, ISO 11135 and ISO 11137-1 (14.27).

Surface.

Both the product and prototype tubing and cuff surface shall be smooth and have no sharp or rough edges. Tubes shall be smooth on external and internal surfaces. There shall be no shoulder material within the lumen. The transitions in the internal diameter shall be tapered IAW ASTM F 1242 section 4.2.1 (14.1). The product should have the markings and symbols in conjunction with symbols and texts from ISO 15223 (ISO, 2007). All tubing (both prototype and product) must also have markings on the exterior to indicate depth of insertion. If the standards referred to in this specification are superseded by an approved revision, the revision shall apply. The product tube must have a radio-opaque blue line which allows for identification of the tube position in an x-ray.

Tubes.

If Murphy's eye and a bevel is provided on the patient end of any tubing for the prototype and product, then all surfaces must be rounded and smooth. All of the features are must be IAW 4.2.1 of ASTM F 1242 (14.1). The prototype and product must consist of a primary tube, which shall maneuver through the trachea, and two secondary tubes, which will be able to lock into the bronchi trees. The primary tube must fit within the average trachea of 16.65 mm diameter and must be able to pass through the vocal cords (14.14). The secondary tubing of the product and the prototype must pass through the trachea and bronchial tree. The tubing must be less than the average left and right lobar bronchi, estimated width of 8.3 mm (14.28). The secondary tubing must also be able to accommodate a child endoscope, which requires the inner diameter to be greater than 3.65 mm. The secondary tubing must also be able to curve 50° with the bronchi branches (14.19). The effective inside diameter of the secondary tubing is determined by Annex B of ISO 16628: 2008, 4.2. The diameter should be expressed and rounded down to the smaller 0.2 mm dimension (14.31). The secondary tubing cuffs and associated pilot balloon of the product shall be entirely colored blue IAW ISO 16628: 2008, 4.3 (14.31). All components of the product including the tracheal tube, inflatable tracheal cuff, bronchial tube, anesthesia breathing circuit, breathing tube support, tracheal/bronchial differential ventilation tube, ventilator tube, cuff spreader, and tracheal tube fixation should be reproducible to meet all FDA classification 2 requirements.

Both prototype and product tubing shall fit the Magill Curve standard bend radius with a maximum limit of 160 mm and minimum limit of 120 mm, which conforms to the shape of the airway with the head held in the neutral position. Curved tubing reduces the chance of kinking during insertion when compared to straight tubing.

Connection.

The connection to the ventilator should not leak, and should stay sufficiently stable and resist being disconnected. The fittings provide means to facilitate grasping of the connector. The prototype and product must be able to attach to the standard male 15 mm conical connector complying with ISO 5356-1 (14.30). Connector sizes for the product are defined based on Table 1 The primary and secondary tubing shall be connected to separate ventilators, which will provide the option to have different pressures in the upper versus the lower lobes of the lungs. There are two types of tracheal tube connectors, straight or curved. For straight connectors, the patient end of the tube gets its length from Table 1, and the connector lumen cannot be smaller than tracheal tube lumen. The curved connectors are usually 60° or 90° and have a minimum connector lumen diameter greater than 80% throughout the connector lumen. It shall not be reduced by more than 10% of the equivalent straight connector. Connectors size should be marked and the markings should be visible during use.

TABLE 1

Tracheal tube connectors - size range and basic dimensions of patient end

| Desigated size (nominal inside diameter) | Inside diameter d (±0.15) | Dimensions in millimeters | |
|---|---|---|---|
| | | Straight connectors - minimum dimension, $l_1$ (effective length)$^a$ (FIG. 2) | Curved connectors - minimum dimension, $l_2$ (effective length)$^a$ (FIG. 3) |
| 2.0 | 2.0 | 9 | — |
| 2.5 | 2.5 | 9 | — |
| 3.0 | 3.5 | 9 | — |
| 3.5 | 3.5 | 11 | — |
| 4.0 | 4.0 | 11 | — |
| 4.5 | 4.5 | 12 | — |
| 5.0 | 5.0 | 12 | — |
| 5.5 | 5.5 | 13 | 10 |
| 6.0 | 6.0 | 13 | 10 |
| 6.5 | 6.5 | 16 | 10 |
| 7.0 | 7.0 | 16 | 10 |
| 7.5 | 7.5 | 16 | 10 |
| 8.0 | 8.0 | 16 | 10 |
| 8.5 | 8.5 | 16 | 10 |
| 9.0 | 9.0 | 16 | 10 |
| 9.5 | 9.5 | 16 | 10 |
| 10.0 | 10.0 | 16 | 10 |
| 10.5 | 10.5 | 16 | 10 |
| 11.0 | 11.0 | 16 | 10 |

$^a$The effective length of the patient end of a tracheal tube connector is that length available for insertion into the tracheal tube.

Murphy's Eye.

The end of the primary tube shall contain a beveled end and include a Murphy's eye, which is a secondary opening that shall allow fluid flow if the primary opening is occluded. Murphy's eye shall be placed on the opposite side of the bevel. It should not be less than 80% of the tube lumen diameter IAW ASTM F 1242 section 6.5 (14.1).

Bevel.

The LID tubing bevel shall have an angle no greater than 48 degrees and no smaller than 28 degrees. The bevel should be oriented according to ASTM F 1242 section 6.4 (14.1).

Cuffs.

Both the primary and secondary tubes must be anchored and sealed with an inflatable cuff. When tested for tracheal seal according to Annex G of ISO 5356:2016, 5.5.6, the cuff shall limit leakage and aspiration of liquids when inflated to internal pressures not exceeding 2.7 kPa (27 cm $H_2O$) (14.27). The cuff must be reliably attached to LID. The product's cuffs should be reliably attached to the tracheal tube IAW ASTM F 1242 Section 5.1 (14.1). The cuffs of the prototype and product shall have a smooth external surface IAW ASTM 1242 regulations. The cuffs must also follow all surface specifications. Cuffs shall not block the murphy's eye. Inflated or deflated cuffs should not interfere with the murphy's eye, or any hole acting as such. Cuff's distance shall be measured by the tip of bevel to the end of merged cuff. Cuffs shall not herniate over lumen in accordance with ASTM F 1242 Cuff Herniation (14.1). Cuffs must be able inflate itself symmetrically and be inspected for bulging and thinning IAW ASTM F 1242 Inflation test (14.1). Every cuff on the prototype and product must inflate symmetrically in the planes perpendicular to the tube and must be mounted on the mandrel. The cuff shall be inflated to 2.5× the outside diameter of the tube. Cuffs shall be inflated by inflation system that will be present in LID tube walls. Cuffs resting diameter shall be assessed IAW ASTM F 1242 Diameter Assessment (14.1) A1.5.

Inflation System.

The inflation lumen in wall of tracheal tube, inflation line, pilot balloon, inflation valve in the product shall not encroach upon the tracheal tube lumen by more than 10% of the inside diameter of the tracheal tube at the point of separation IAW ISO 5361:2016, 5.6.1 (14.27). LID inflations line length shall extend past primary tube greater than 3 cm. If the inflation line is clamped, it shall be able to reopen. The inflation must be IAW ASTM F 1242 Leak Test. LID must have a method of transporting ventilated air into the body. The inflation line diameter shall be less than 2.5 mm. The inflating tube shall have a pilot balloon and/or other device to indicate inflation/deflation status of the cuff IAW ISO 5361:2016, 5.6.3 (14.30). The one-way valve that is connected to pilot balloon shall have an inlet that accepts a male luer syringe tip. The inlet diameter must not be greater than 4.4 mm, contain a 6% (Luer) taper, and has a minimum length of engagement of 4.7 mm. ISO 594-1 (14.3). The LID must be capable of receiving a maximum pressure of 40 cm$H_2O$/30 mmHg and provide a minimum volume of 10 mL/kg at intervals of 26 bpm (breaths per minute).

Example 2

Design Solutions

Bronchial Tubelets.

Figure 12:
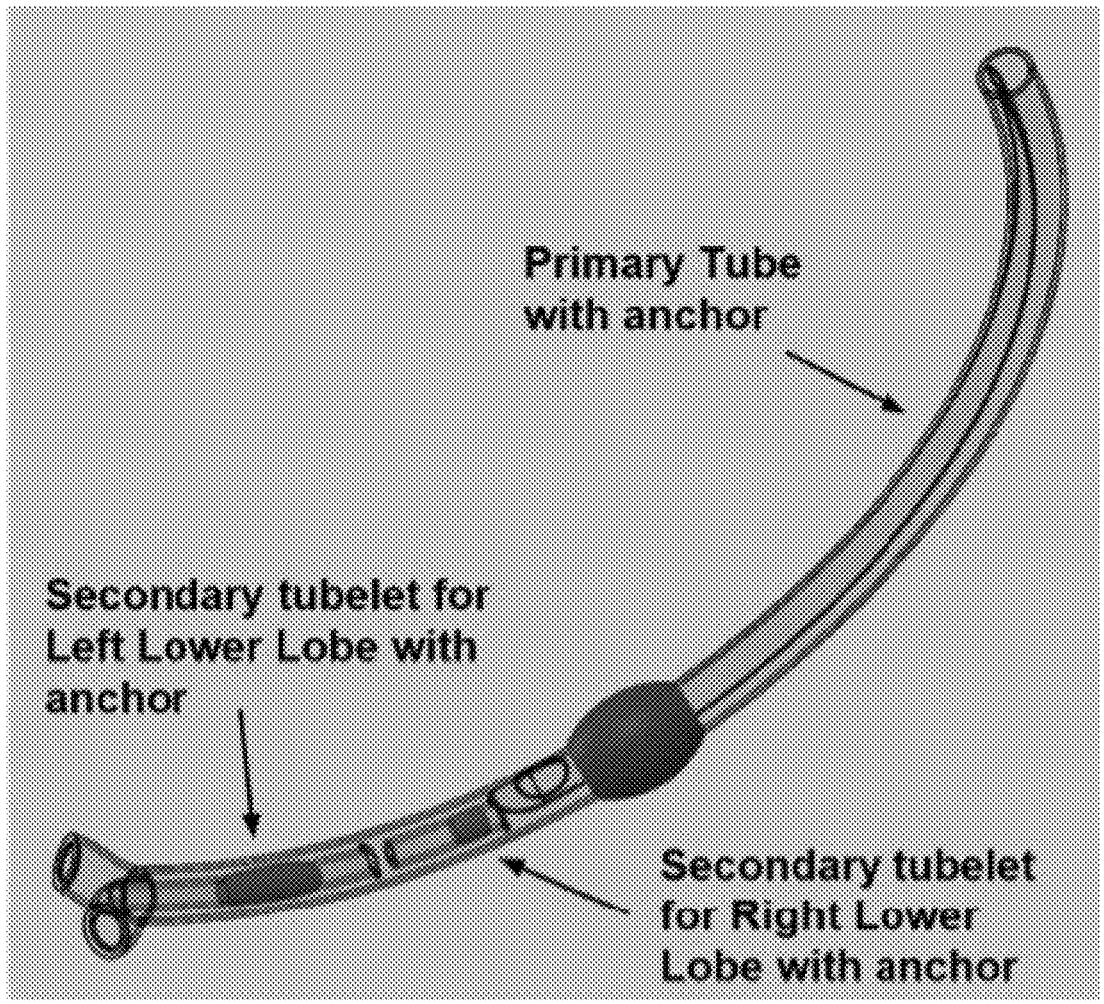
FIG. 12. Illustration of bronchial tubelets concept showing primary tube, secondary tubelets, and cuffs.
Figure 13:
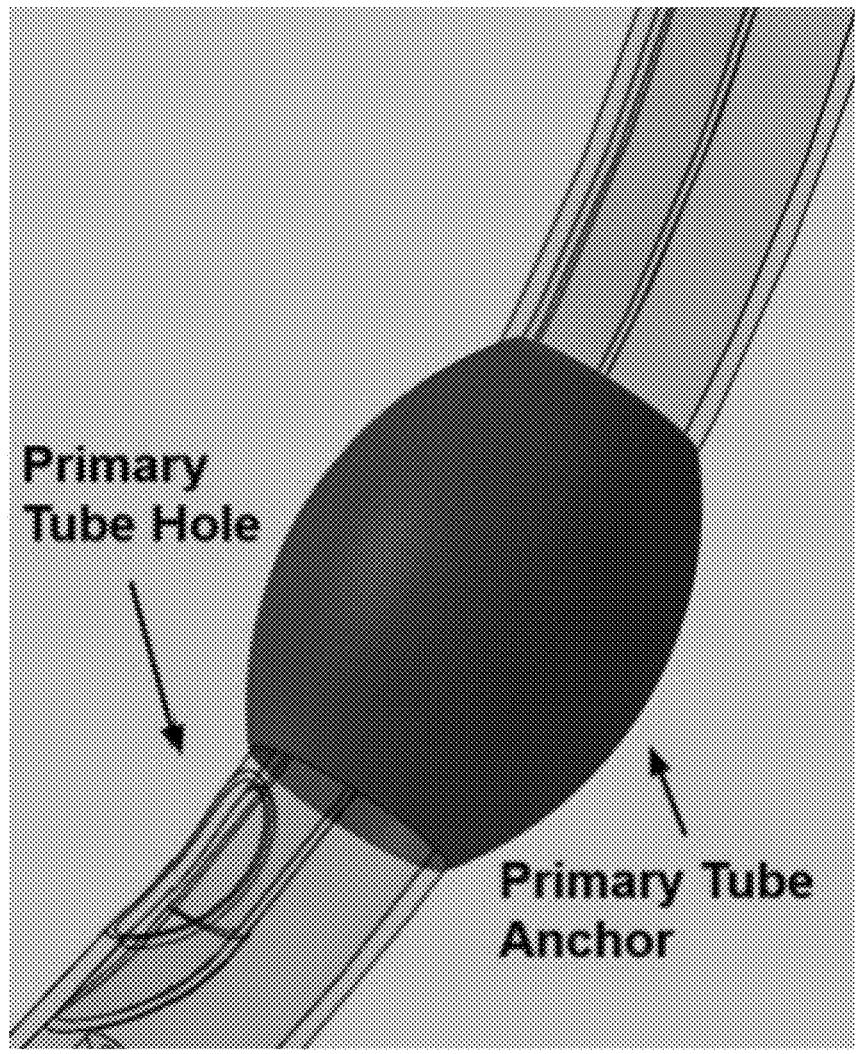
FIG. 13. Illustration of the anchoring system for the bronchial tubelet concept.
Figure 14:
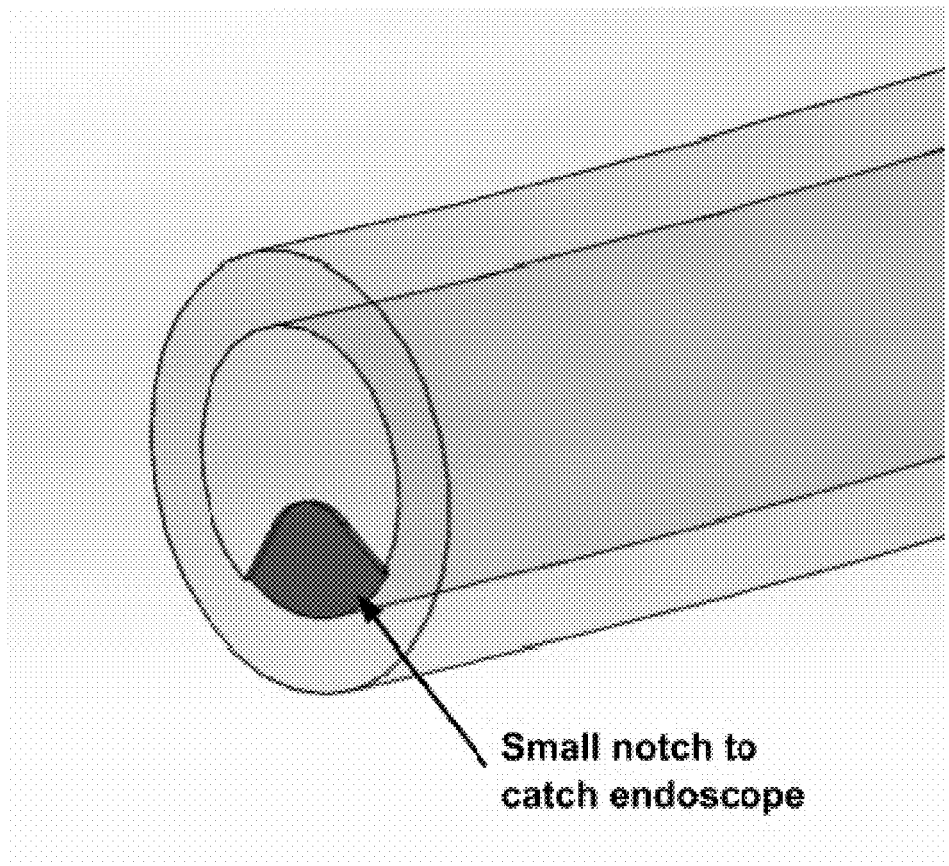
FIG. 14. Illustrates catching mechanism for bronchial tubelets concept.

The Bronchial Tubelets design developed a creative solution to the compact problem of multiple tube diameters within the trachea. Bronchial Tubelets used two small tubelets to act as the Secondary tube. FIG. 12 shows how both Primary tube and Secondary tubes are assembled. The method of use for the Secondary tubelets is referred to as "stacking". This specific use of the tubes allow the design to avoid the dimensional constraints of the trachea. This means that the team was able to make adjustments to the Secondary tubelets without changing the dimensions of the Primary tubes largest diameter. This "stacking" method refers to how the Primary tube and Secondary tubelet diameters are in their own respective horizontal plane within the Primary tube. And in this sense that each of those respective planes are stacked along the axis of the Primary tube. The Bronchial Tubelets incorporates a Primary tube, allowing air flow to the upper lobes of the lungs and Secondary tubelets that provide variable pressure to the lower lobes of the lungs. The Primary tube delivers air flow through the hole along the surface, as shown in FIG. 13. Above the hole shown, is the anchoring cuff that allows the Primary tube to be anchored and isolate airflow. Once the primary tube is properly placed within the patient's trachea, the user could then decide if the patient is in need of further lung isolation. If the user would like to further isolate the lung lobes, all they would have to do is guide an endoscope within the Primary tube to reach the Secondary tubelets. Once the endoscope and Secondary tubelets meet, the user would then need to pass the endoscope through the first Secondary tubelet, designed to go into the right lower lobe, and place the scope within the Secondary tubelet closest to the bottom. This bottom Secondary tubelet, like all others, is designed to have a small "notch" or film within the cross-section of the tubelet, shown in FIG. 14.

To maneuver and place the Secondary tubelets, all user would need to do is push on this film and lead the Secondary tubelet with the endoscope to the proper placement, within the lower left section of the bronchial tree. Once the first Secondary tubelet is placed, the user would then need to retract the endoscope and repeat the process for the Secondary tubelet meant for the lower right bronchial tree. Overall the Bronchial Tubelets provide a creative solution to the dimensional constraints and specifications defined for the team's project.

For the Bronchial Tubelets, fluid analysis was conducted to be sure that the ventilator could produce the right amount of air to the respective sections of the lobes. The breathing rate to volumetric flow rate and Reynolds number have been calculated, which lead to the required velocity through each cross sectional area. The breathing rate was assumed to be 18 breaths per minute. Using this parameter and a constant volumetric flow rate across all lower lobes, velocity of the largest diameter, Reynolds number, and friction factor was calculated for the Bronchial Tubelets. The calculations were based off common standards such as density of air, dynamic viscosity of air, and standard atmospheric air pressure. One of the most significant qualities calculated was reynolds number, which clarified that the flow within the tube can be assumed to be laminar. With the standards and foundational terms for pipe flow calculated, the team developed the significant qualities of the flow needed within the Bronchial Tubelets such as velocity and pressure drop. Table 2 shows the listed values for different areas within the Bronchial Tubelets. Inner Tubelet area refers to the inner diameter of the Secondary tubelets, Inner area of the Primary tube refers to the inner diameter of the Primary tube, and Primary Area-Tubelet Area refers to the remaining area between the outer diameter of the tubelet and inner diameter of the Primary tube.

Bronchial Tubelet's secondary tubes tube will require a high pressure drop because of its small diameter.

The Bronchial Tubelets design was intended to meet all specifications required for the Lobe Isolation Device. But the design itself required considerable constraints in designing to allow the feasibility of the device. Most of these constraints were developed into design-based specifications for the Bronchial Tubelets. The specifications could be categorized into Secondary tubelet specifications and Bronchial Tubelets design specifications. The Secondary tubelet design specifications were generated as a precaution for design functionality and patient security. The specifications included applying specified lengths to each Secondary tubelet. This specified length allows the Secondary tubelets to safely reach the isolation points of the bronchial tubelets. Another specification would be the need for the Secondary tubelets to have a unique inflation system for their anchors. This unique inflation system would allow the Secondary tubelets to each have their own pressure or volume control, as well as allow retracting from their previous placement. The idea of using tubelets to be placed was very innovative thinking, but the free connecting tubelets did pose a serious risk. The previously mentioned specification would require the Secondary tubelets to have a film or some other connection, that would allow the user to inflate, deflate, and de-anchor the Secondary tubelets so they may be retrieved out of the patient.

The next category of specifications were generated from the overall design and needs of the concept's functionality. The Bronchial Tubelets needed to have the Secondary tubelets inside the Primary tube and placed underneath the Primary tube's anchor and opening. The last specification for the concept would be the a specified clearance for the Secondary tubelets so they shall not be loose within the Primary tube. The last two specifications allow the Bronchial Tubelets to stay within a tolerable range of functionality, and feasibility. These specifications and constraints generate various complexity in manufacturing, as well as product testing and reliability.

Simple Tracheal Tube.

The Simple Tracheal Tube was designed to be a simple solution using geometric variances to acquire specified results. The simplicity of the Simple Tracheal Tube design comes from the need of fewer parts for use. The Simple

TABLE 2

Velocities and pressure drops for the tubes and tubelets.

|  | Velocity Required | Velocity Pressure | Pressure drop |
|---|---|---|---|
| Inner Area of Tubelet |  | 2.54 cmH2O | 1551 cmH2O |
| 10.75 mm^2 |  | 1.87 mmHg | 1141 mmHg |
| 1.08E−05 m^2 | 20.151 m/s | 248.72 Pa | 1.52E+05 Pa |
| Inner Area of Primary Tube |  | 0.05 cmH2O | 10.8 cmH2O |
| 78.54 mm^2 |  | 0.03 mmHg | 7.9 mmHg |
| 7.85E−05 m^2 | 2.759 m/s | 4.66 Pa | 1.05E+03 Pa |
| Primary Area-Tubelet Area |  | 0.13 cmH2O | 39.4 cmH2O |
| 46.73 mm^2 |  | 0.10 mmHg | 29.0 mmHg |
| 4.67E−05 m^2 | 4.636 m/s | 13.17 Pa | 3.86E+03 Pa |

Figure 15:
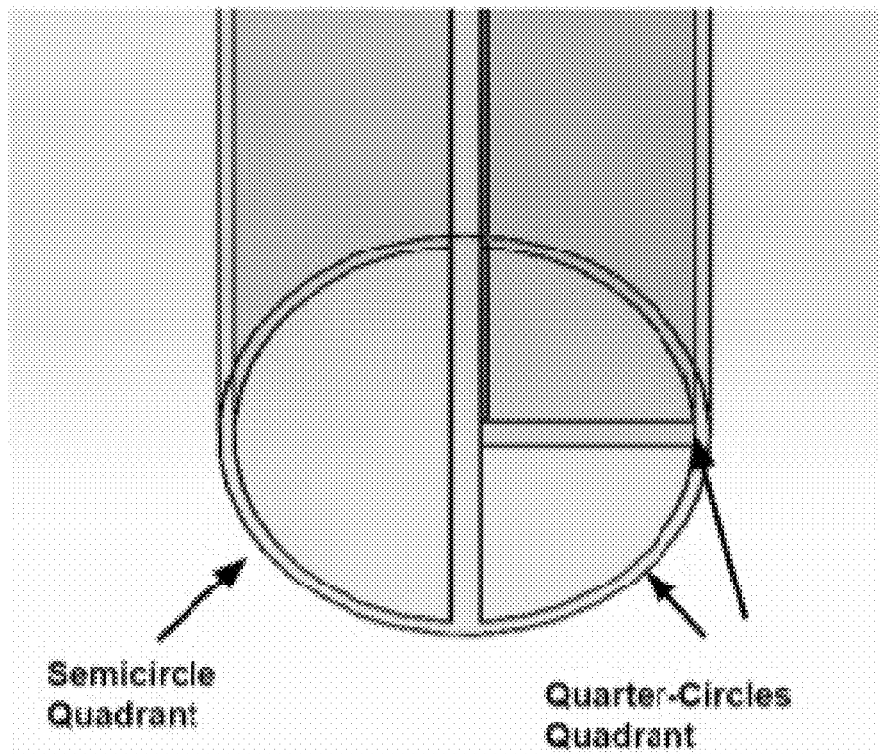
FIG. 15. Cross sectional view of simple tracheal tube.
Figure 16:
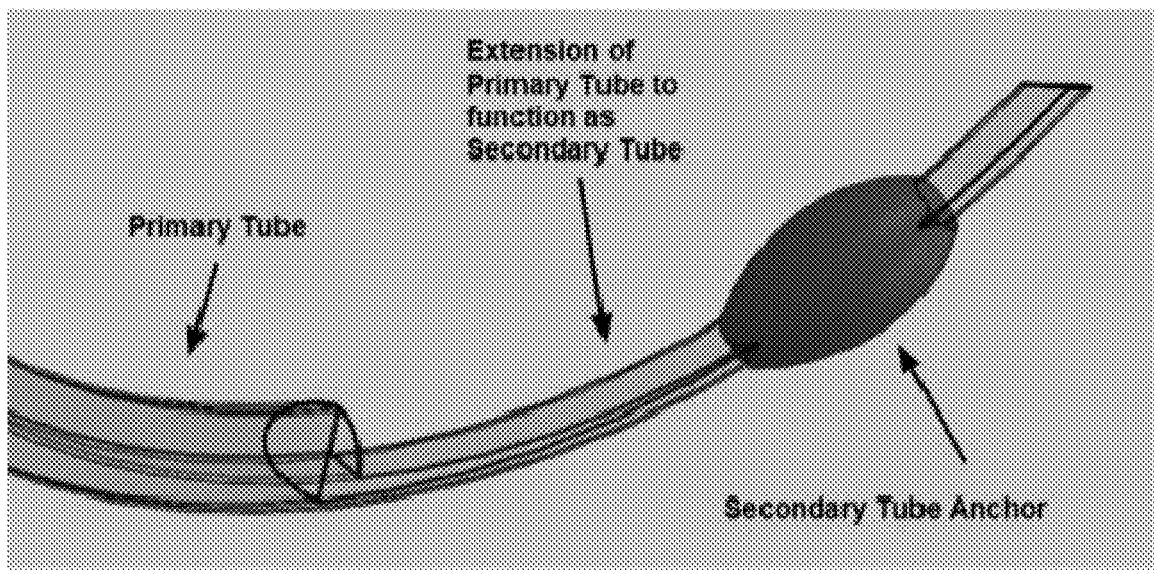
FIG. 16. Illustration of extension of primary tube into bronchial tree to act as secondary tube.

The most significant item to take away is the velocity required to provide the necessary flow rate calculated. The velocity calculated does not show any significant error because it followed the pipe flow concept of the inverse relationship between velocity and diameter that has a constant flow rate. The high required velocity shows that the Tracheal Tube only requires two tubes, this is because the acting primary tube dual functions as the secondary tube. That leaves only one more tube needed to give the design dual Secondary tubes. One significance of this design comes from the change in cross section, allowing the Primary tube to narrow itself down and fit within the bronchial trees specifications. The initial split from the top of the tube, cutting the round cross-section of the tube into two semi-circles. Once the tube has hit the specified length of bifurcation in the trachea, one of the semicircle cross-sections separates into two quarter-circles. FIG. 15 shows the final cross section of the Primary tube once it reaches the trachea bifurcation. FIG. 16 shows how one of the quarter-circles stops at the bifurcation of the trachea, and the other extends down acting as the Secondary tube. The end result is one semi-circle cross-section that provides air pressure to the upper lungs, one quarter-circle extended tube that provides air pressure to the left lower lobes of the lungs, and one last quarter-circle opening that will allow a separate Secondary tube to be inserted for the lower right lobes of the lungs. The Simple Tracheal Tube design allows the insertion of three different tubes by reducing the cross section of both Primary and Secondary Tubes and geometrically combining their reduced diameters to still keep the compactness necessary.

The fluid analysis of the Simple Tracheal Tube was conducted to be sure that the ventilator could produce the right amount of air to the respective sections of the lobes. The breathing rate to volumetric flow rate and Reynolds number have been calculated, which lead to the required velocity through each cross sectional area. The breathing rate was assumed to be 18 breaths per minute. Using this dependant variable and a set volumetric flow rate, velocity of the Primary tube, Reynolds number, and friction factor for the design. To calculate these terms standard environmental effects were assumed for density of air, dynamic viscosity of air, and atmospheric air pressure.

Table 3 below shows the summary of calculations for the velocity and pressures required for the Simple Tracheal Tube Concept. The highest velocity of air required to properly ventilate one section of the lungs is maintained from the small placeable tube at 19.617 m/s with a velocity pressure of 235 Pa, which is well within the limits of a standard hospital ventilator.

TABLE 3

Simple tracheal tube required velocity and pressure drop.

| | Velocity | Velocity Pressure | Pressure drop |
|---|---|---|---|
| Inner Area of Half | | 0.25 cmH2O | 141.2 cmH2O |
| 34.27 mm^2 | | 0.18 mmHg | 103.9 mmHg |
| 3.43E−05 m^2 | 6.322 m/s | 24.48 Pa | 1.38E+04 Pa |
| Inner Area of Quadrent | | 1.37 cmH2O | 309.7 cmH2O |
| 14.63 mm^2 | | 1.01 mmHg | 227.8 mmHg |
| 1.46E−05 m^2 | 14.805 m/s | 134.25 Pa | 3.04E+04 Pa |
| Small Tube inner area | | 2.40 cmH2O | 1450.1 cmH2O |
| 11.04 mm^2 | | 1.77 mmHg | 1066.6 mmHg |
| 1.10E−05 m^2 | 19.617 m/s | 235.71 Pa | 1.42E+05 Pa |
| Quadrent-Tube Space | | 2.22 | 1312.7 cmH2O |
| 11.49 mm^3 | | 1.63 | 956.6 mmHg |
| 1.15E−05 m^3 | 18.851 m/a | 217.67 | 1.29E+05 Pa |

Figure 17:
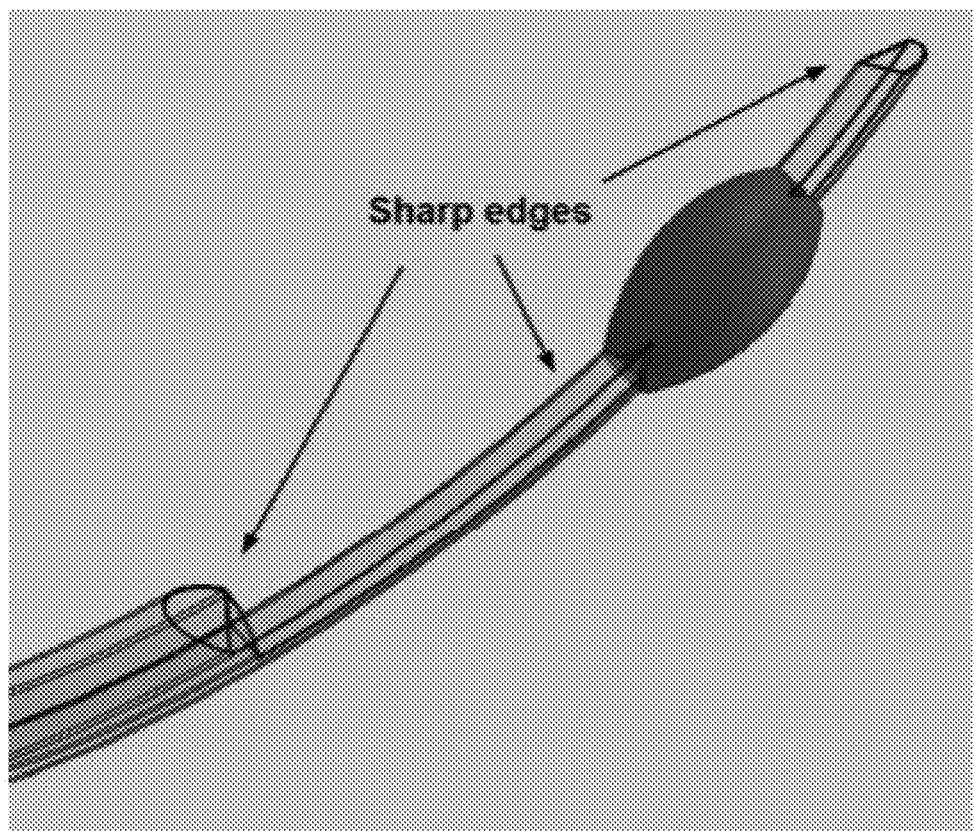
FIG. 17. Illustration of edges generated by primary tube extrusion in simple tracheal tube concept.

The Simple Tracheal Tube was designed with the intent of accomplishing all specifications of the project, but upon further inspection conceptually, the concept needed to abide by even more specifications. These specifications were generated specifically for this concept to assure the effectiveness and underlying confirmation of the designs ability to complete the project purpose. The Simple Tracheal Tube was required to have a specific length, that would allow the design to be widely used and not be dependent on the patient. This length is very critical because of the varying length of the trachea and bronchial trees. The Simple Tracheal Tube also uses complex geometry as a solution to the project's purpose. This complex geometry generates two concerns of functionality, which caused the team to resolve these concerns by setting specifications. One of the specifications requires ease of sliding when inserting the Secondary tube to isolate the lower right lung, and the other requires the edges of the Primary and Secondary tube to be filleted to avoid any sharp edges. Both specifications were amended to fit the specific geometric qualities of the Simple Tracheal Tube, for example, in FIG. 17 the extruded section of the primary tube creates a sharp edge both on the end of the tube and along the extruded length of the tube. The other specification generated based of the geometry of the design would be the tightness of both quarter quadrants inside the primary tube. Even though one of the quadrants will support the insertion of a Secondary tube, the clearance was very concerning for the team. These two geometric obstacles were the main reasons for risk of functionality behind the Simple Tracheal Tube.

Backwards Compatible Tracheal Tube.

Figure 18:
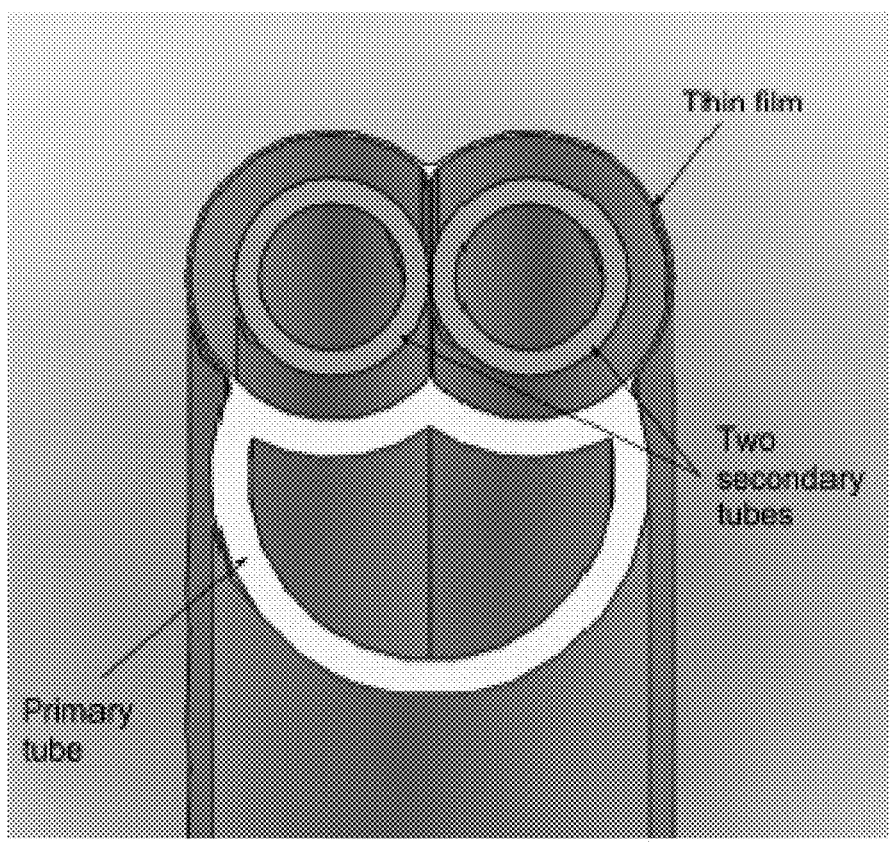
FIG. 18. Illustration of backwards compatible tracheal tube.

The Backwards Compatible Tracheal Tube gets its name from its ability to be used as either an endotracheal tube, ventilating the entirety of the lungs, or a lobe isolation device. It consists of an atypically shaped primary tube which cups the secondary tubes to lessen the outer diameter when they are placed, as shown in FIG. 18. A thin film attached to the primary tube serves as a guidance tool for the secondary tubes if they are inserted. Initially, only the primary tube is inserted without the secondary tubes as shown in FIG. 19A. The thin film collapses and the outer diameter of the tube is significantly reduced allowing for easy insertion through the vocal cords. If ARDS is detected in the patent or lobe isolation is needed in any way, the secondary tubes can be placed, as shown in FIG. 19B. The secondary tubes travel through the thin film to their respective bronchi branches and lock into place. The outer diameter expands with the secondary tube insertion, but the vocal cords can expand without harming the patient; it is the initial insertion that can harm the vocal cords which is one of the main features that makes this concept so superior.

Other advantages of this concept involve its ability to find the proper placement of the secondary tubes. This is the only concept that allows for length adjustments to be made by the user. Bronchial Tubelets has a defined length for each of the tubelets so placement would be incredibly difficult. Simple Tracheal Tube allows for length adjustment of one of the secondary tubes, but the other is at a set length.

Versatility is one of the most important aspects of this project, and this concept meets that function very well with its ability to switch between regular endotracheal tube and lobe isolation with merely the placement of two tubes. Bronchial Tubelets can be used as an endotracheal tube, but the tubelets would block fluid flow, and after the tubelets would have been placed, it would be difficult to retrieve them, and there is always the chance that the tubelets could get stuck. The Simple Tracheal Tube would be incredibly difficult to be used as an endotracheal tube because of the extended quadrant left to dangle in the bronchi branches.

The simplicity of this design was also an important consideration. With only a primary tube, secondary tubes, and openings for the secondary tubes, this concept has full functionality while saving as much space as possible. The Bronchial Tubelets concept involves moving parts, requires very specific lengths for the tubelets, has a complex way of removing the tubelets, and may be the most complex concept generated. The Simple Tracheal Tube is simplistic as the title states, but its other qualities do not stack up against the Backwards Compatible Tracheal Tube.

In order to see what is required for each patient, volumetric flow rates were calculated using average tidal volume, respiratory rate, and a 1:3 I:E—Inspiratory to Expiratory ratio and assuming a 6 foot male. A volumetric flow rate for the entire lungs was calculated as 832 mL/s. The sections of the lungs were calculated by the percent composition of each lobe. The right lower lungs require 237.7 mL/s, the left lower need 198.1 mL/s, and the total upper requires 316.91 mL/s. The average ventilator can produce at least 46 kPa of pressure. By taking the cross sectional area (A) of each individual tube, and the required volumetric flow rates (Q) for each section of the lung, the required velocity (v) for each tube to reach that volumetric flow rate was calculated assuming straight pipe flow:

$$v = \frac{Q}{A} \quad (1)$$

From the required velocity, the dynamic pressure (q) could be calculated:

$$q = \frac{\rho v^2}{2} \quad (2)$$

In order to calculate the actual pressure drop through the tube, a friction factor had to be calculated. In order to find the friction factor, the fluid flow had to be defined as laminar or turbulent. The Reynolds number turned out laminar, and the friction factor could be calculated:

$$Re = \frac{\rho v D}{\mu} \quad (3)$$

$$f = \frac{64}{Re} \quad (4)$$

Once the friction factor is found, the pressure drop can be calculated:

$$\Delta P = f \frac{L}{D} \frac{\rho v^2}{2} \quad (5)$$

Research shows that the standard ventilator can produce a pressure drop of 46 kPa. With this information, it can be assumed that if the pressure drops through this concepts tubes are less than that, then the ventilator can provide enough pressure to get the required breathing rate to the patient.

TABLE 4

Analysis of the drop in pressure required for each tube of the backwards compatible tracheal tube.

|  | Velocity Required | Dynamic Pressure | Pressure drop |
|---|---|---|---|
| Primary Tube Only 38.6 mm^2 |  | 2.902 cmH2O 2.134 mmHg | 328 cmH2O 241 mmHg |

TABLE 4-continued

Analysis of the drop in pressure required for each tube of the backwards compatible tracheal tube.

|  | Velocity Required | Dynamic Pressure | Pressure drop |
|---|---|---|---|
| 3.86E-05 m^2 | 21.55 m/s | 254.56 Pa | 32189 Pa |
| Right Secondary Tube |  | 2.235 cmH2O | 340 cmH2O |
| 12.56637061 mm^2 |  | 1.644 mmHg | 250 mmHg |
| 1.26E-05 m^2 | 18.92 m/s | 219.15 Pa | 33316 Pa |
| Left Secondary Tube |  | 1.552 cmH2O | 260 cmH2O |
| 12.56637061 mm^2 |  | 1.142 mmHg | 191 mmHg |
| 1.26E-05 m^2 | 15.76 m/s | 152.21 Pa | 25482 Pa |

As shown in Table 4, the highest pressure required for this concept is 33 kPa which is within the ventilators limits, which validates the feasibility of the flow rates in this concept.

One important specification associated with this project is dimensional certainty, locking and sealing, and ventilating. The dimensional dilemma associated with this project came from the fact that the entire device has to be able to comfortably fit within an average human trachea with a 16 mm inner diameter. Each tube in this device also has to be able to be guided with an endoscope with an outer diameter of 3.65 mm.

The primary tube design consists of an outer diameter of 12 mm and an inner of 10 mm giving it a thickness of 1 mm. The primary tube has small semi circles cut out for the secondary tubes to sit comfortably as shown in FIG. 20. The space in the center of the primary tube has a space of 6.33 mm which is more than enough room for an endoscope to glide through it. For some tolerance, an inner diameter of 4 mm was chosen for the secondary tubes, they each have a thickness of 0.7 mm giving them an outer diameter of 5.4 mm each. When the secondary tubes are placed through the thin film, the entire device has an outer diameter of 13.74 mm which can fit comfortably in the human trachea. The ability to switch so easily between an endotracheal tube and a lobe isolation device and its dimensional ease are two huge factors in the consideration of this project. Both are important for full functionality in our specifications and this concepts meets both exceedingly well.

Figure 21:
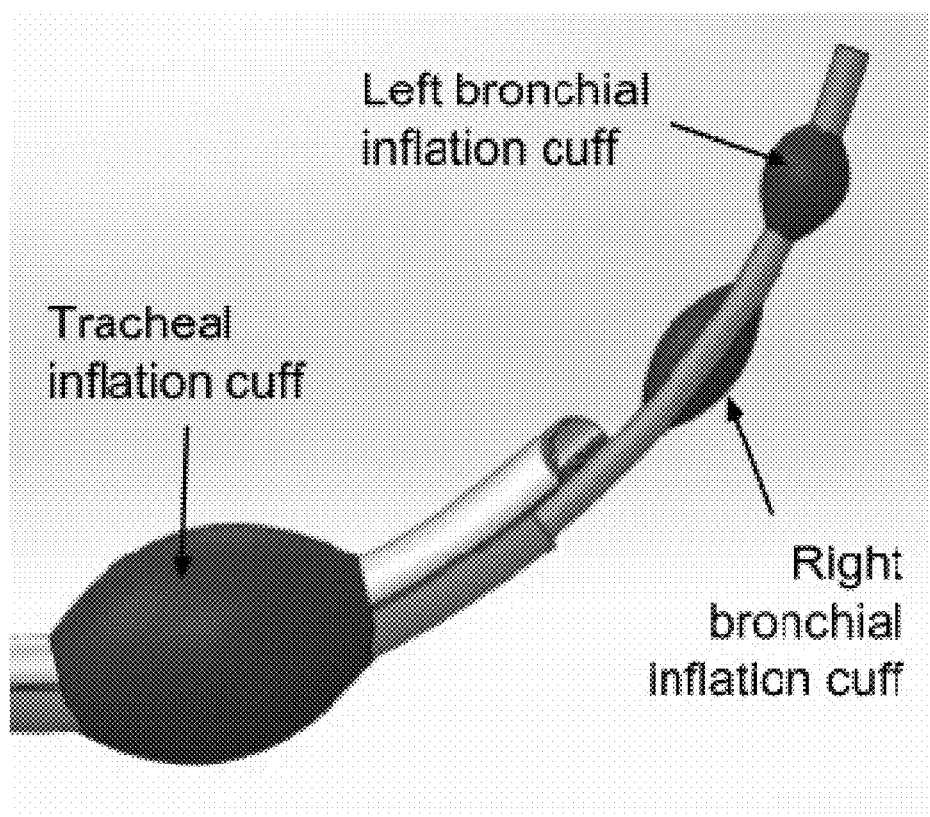
FIG. 21. Illustrates inflation cuffs of primary and secondary tubes.

To achieve lung ventilation in any way, a locking device is required to block airflow from escaping through the trachea and exiting the mouth, which would render the product useless. An inflation cuff is capable of serving this purpose. Inflation cuffs have been used in endotracheal tubes for a long time because not only do they prevent air from escaping, but it locks the tube in place within the trachea by pressing against the walls. The same concept can be applied to the bronchi. FIG. 21 shows the inflation cuffs on their respective tubes. Using these cuffs, the secondary tubes can lock into the bronchi and supply airflow to the lower lobes, while blocking it from escaping to the upper lobes. The primary tube also ventilates the upper sections through the upper branches of the bronchi with the cuffs preventing that flow to the lower sections.

It should be noted that this concept is the only one that allows individual placement of both secondary tubes to find the optimal placement. Each bronchial tree is different for each person, and if a tube is not long enough to reach the optimal part of the patient's tree, the cuff could potentially not lock completely, or allow air to pass, rendering the lobe isolation useless.

Example 3

An Example of a Lobe Isolation Device

Figure 22:
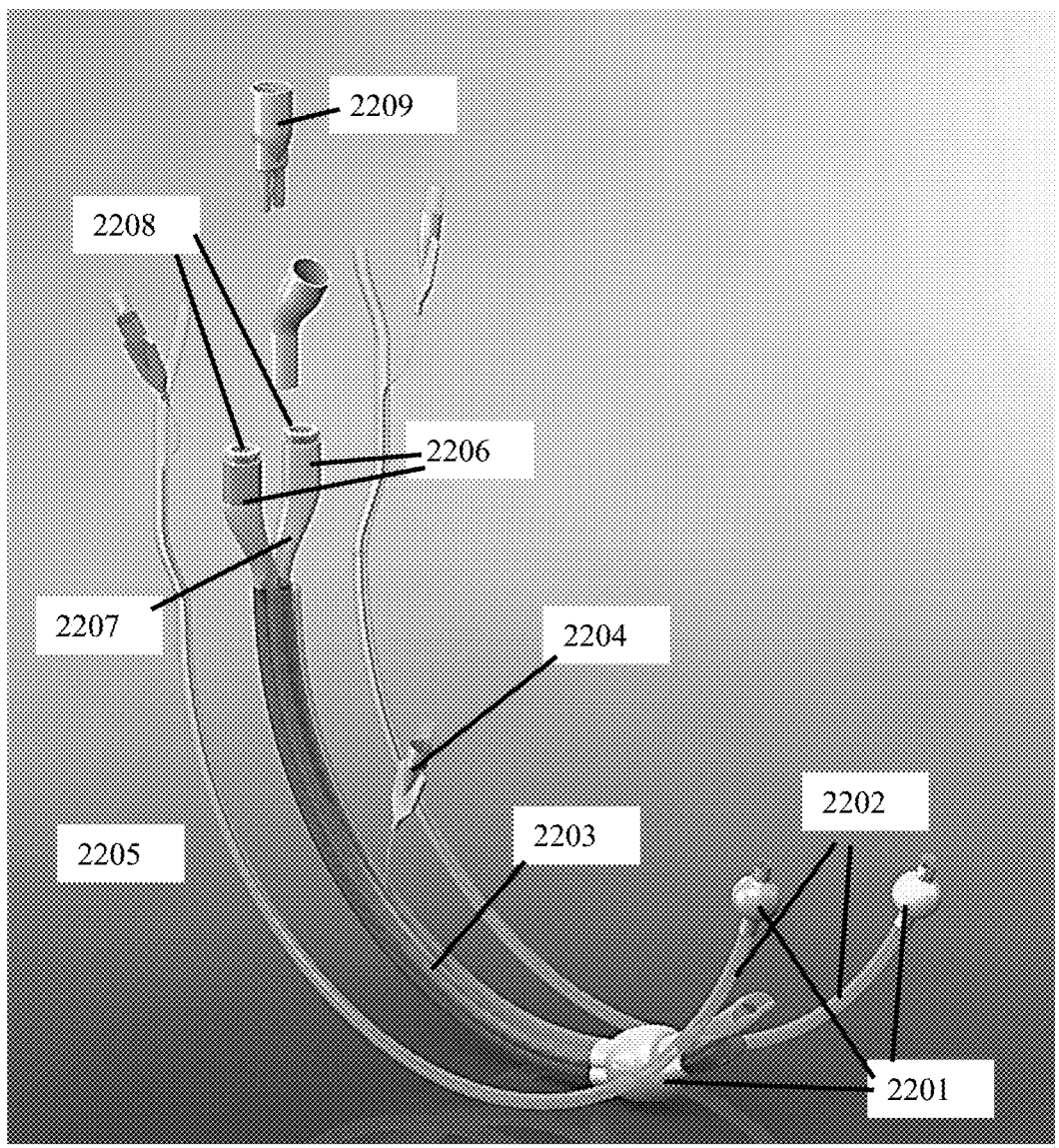
FIG. 22. Illustration of an example of a fully assembled lobe isolation device.
Figure 23:
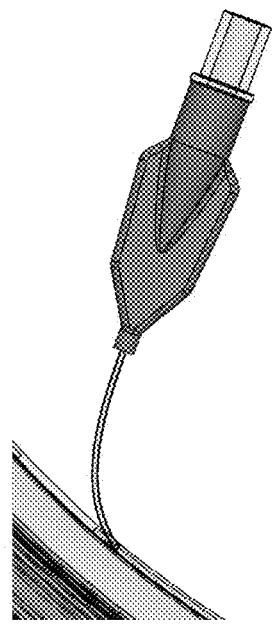
FIG. 23. Inflation Line.
Figure 24:
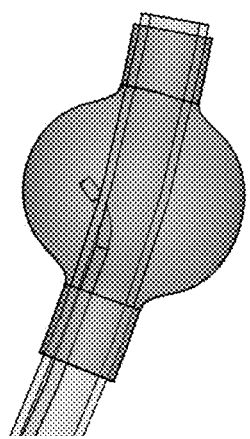
FIG. 24. Cuff Diagram.

A prototype can include three orally inserted plastic tubes that pass through the trachea, which will maintain an unobstructed passageway to deliver oxygen and anesthesia to the lungs. The primary tube is designed to ventilate the entire lungs when used individually. When secondary plastic tubes are inserted, unobstructed passageways to the left and right lower lobes of the lungs are formed. The capability of pressure and volume control of the separate lung lobes reduces the risk of injury to patients who suffer from pulmonary disease, when compared to standard endotracheal tubes. Additionally, the multi-purpose product will allow physicians to dynamically change function depending on the state of the patient's need. FIG. 22 illustrates one example of a fully assembled Lobe Isolation Device (LID).

TABLE 5

Labeled parts of LID based on FIG. 22

| Part No. | Description |
|---|---|
| 2201 | Inflation Cuffs. Blue is primary cuff, yellow is left secondary cuff and red is right secondary cuff |
| 2202 | Secondary tubing for left lower lobe and right middle and lower lobes. |
| 2203 | Primary tube |
| 2204 | One-way valves for primary and secondary tubes. |
| 2205 | Thin plastic to hold the secondary tubes to the primary tube |
| 2206 | Yellow and red markings to indicate placement for left and right secondary tubing |
| 2207 | Primary connector. Attaches the primary tubing to the ventilator. |
| 2208 | Flip-top style, silicon, suction port lids |
| 2209 | Secondary connector. Attaches the secondary tubing to the ventilator. |

Performance specifications. The primary tube must fit within the average tracheal diameter of 16.65 mm and must be able to pass through the vocal cords. The secondary tubing must be less than the average left and right lobar bronchi, estimated width of 8.3 mm, but larger than the 3.65 mm diameter of a child endoscope. All tubing shall fit the Magill Curve standard bend radius of 120 mm to 160 mm to conform to the shape of the airway and reduce chances of kinking during insertion. The LID must perform with a maximum pressure of 40 cmH$_2$O/30 mmHg and provide a minimum volume of 10 mL/kg at intervals of 26 Breaths per Minute (BPM).

Inflation System:

The inflation and deflation of an anchoring cuff is achieved by inserting a Luer syringe into the Luer connector of the inflation system, which contains a one-way valve. Pushing the handle of the syringe forces air through the inflation line that leads under the cuff, thus increasing the volume of air. The associated pilot balloon allows the user to visually detect whether there is a leak in the system by maintaining a fully inflated state. The increase in volume of the cuffs will anchor the tubing to the wall of the trachea or lobar *bronchus* of the patient by forming a pressure seal. The yellow markings of the left inflation cuff and the red markings of the right inflation cuff, indicate the proper anatomical side for the placement of the secondary tubes. Deflation of a cuff reduces the pressure and releases the anchor. In the prototype, the inflation tubes will be threaded and sealed within the secondary tubes to allow pressure control of the cuffs. (see FIG. 23-26)

Secondary Tubing:

If ARDS symptoms occur, further assistance can be provided by the secondary tubes. The secondary tubes should be used for an additional breathing aid and can be removed when the patient no longer needs breathing assistance. Due to the smaller internal diameter of the secondary tubes, it would be best to place a child endoscope inside of the tubing as the visual guidance tool. The markings that are present on the cuffs of the secondary tubing to indicate if the tube is used for the left or right side of the lungs. The tube with the red markings should be used for the right middle and lower lobes. The tube with the yellow markings should be used for the left lower lobe. In order for the cuffs to make complete contact with the patient and form a seal, the tubes need to be anchored in the correct location. The secondary tube meant for the left lower lobe should be anchored at the approximate midpoint of the left lower lobar bronchus. The secondary tube meant for the right middle and lower lobes should be anchored after the right upper lobe bronchus but before the right middle lobe bronchus (*Bronchus intermedius*). Either the left or the right secondary tube may be inserted first. The left secondary tubing is roughly 3-4 cm longer than the right secondary tubing. Anatomically, the right secondary bronchus is shorter when compared to the left, due to the additional division from the middle lobe of the right lung. Given a 40 cm H$_2$O pressure supplied by the ventilator, the 4 mm inner diameter left and right tracheal tubes are calculated to be able to supply 7.28E-4 m$^3$/s and 7.64E-4 m$^3$/s breathing rates respectively; these are much higher than the required 1.98E-4 m$^3$/s and 3.17E-4 m$^3$/s required for their respective lobes.

TABLE 6

Left Secondary Tube Calculations
Left Secondary 0.004M

| Area | Velocity from Ventilator Pressure | Producible Breathing Rate |
|---|---|---|
| 0.01257 mm$^2$ 1.26E-05 m$^2$ | 57.901 m/s | 7.28E-04 m$^3$/s |

TABLE 7

Right Secondary Tube Calculations
Right Secondary 0.004 m

| Area | Velocity from Ventilator Pressure | Producible Breathing Rate |
|---|---|---|
| 0.01257 mm$^2$ 1.26E-05 m$^2$ | 60.760 m/s | 7.64E-04 m$^3$/s |

TABLE 8

Right Middle and Lower Lobe Required Breathing Rate
Right Lobes

| | | |
|---|---|---|
| Volumetric flow rate | 3.17E-04 | m$^3$/s (AV) |
| vD | 0.62760 | m$^2$/s |
| Re | 41,766.46 | Turbulent |
| Friction Factor | 0.022 | 64/Re for Laminar |

TABLE 9

Left Lower Lobe Required Breathing Rate
Left Lobes

| | | |
|---|---|---|
| Volumetric flow rate | 1.98E−04 | m^3/s (AV) |
| vD | 0.23161 | m^2/s |
| Re | 15,413.33 | Turbulent |
| Friction Factor | 0.02 | 64/Re for Laminar |

Figure 28:
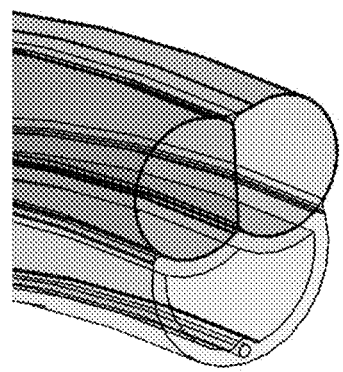
FIG. 28. Primary Tube Opening.
Figure 29:
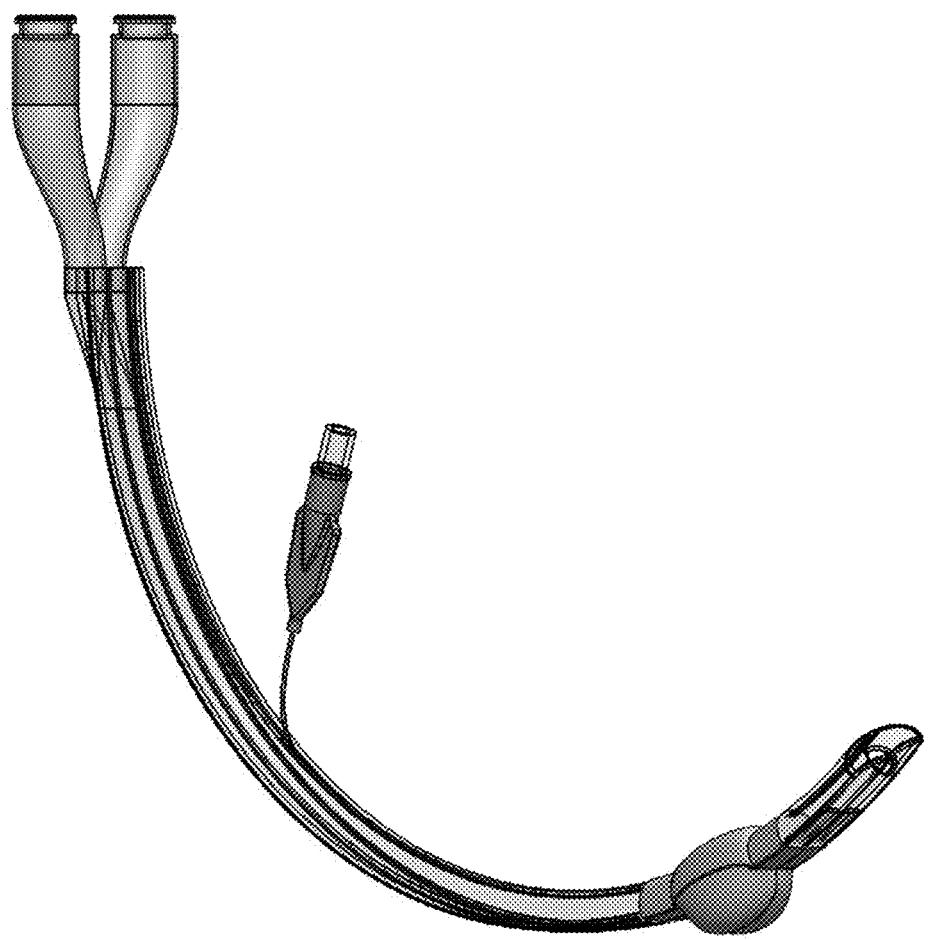
FIG. 29. Primary Tube Without Secondary Tubes.

Primary Tubing:

Due to the Primary Tube's unique shape, an idealized circular diameter was calculated to be equivalent to 7.97 mm. Assuming a ventilator pressure of 40 cm $H_2O$, the area from the idealized calculated to be 49.95 mm². With these dimensions, the tube can provide a breathing rate of 3.93 E-3 $m^3/s$, which is above the required 8.32 E-4 $m^3/s$ that the entire lungs would need to provide sufficient oxygenation. (see FIG. 28)

TABLE 10

Primary Tube Calculations
Primary 0.00797 m

| Area | Velocity from Ventilator Pressure | Producible Breathing Rate |
|---|---|---|
| 49.95 mm^2 5.00E−05 m^2 | 78.697 m/s | 3.93E−03 m^3/s |

TABLE 7

Lung required breathing rate
Entire Lungs

| | | |
|---|---|---|
| Volumetric flow rate | 8.32E−04 | m^3/s (AV) |
| vD | 0.63057 | m^2/s |
| Re | 41,964.15 | Turbulent |
| Friction Factor | 0.023 | 64/Re for Laminar |

Figure 30:
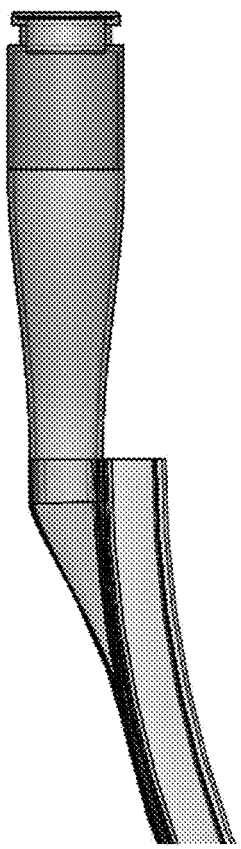
FIG. 30. Primary tube with Suction Port Lids keeping the thin film open for easy insertion.
Figure 31:
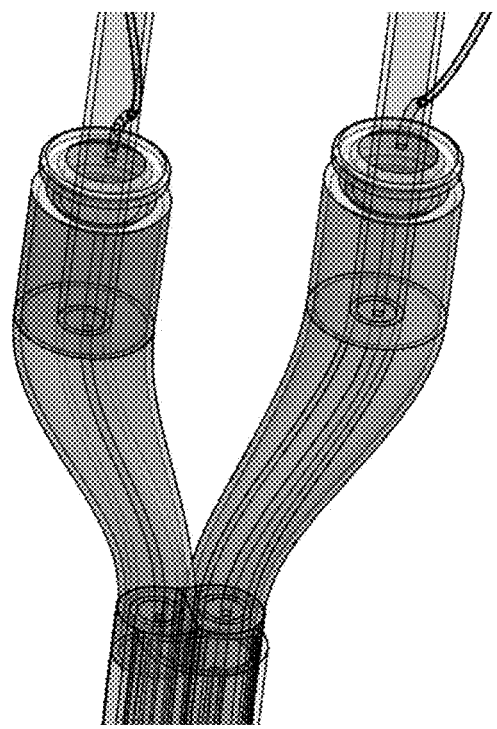
FIG. 31. Suction Port Lids with Secondary Tubes Inserted.
Figure 32:
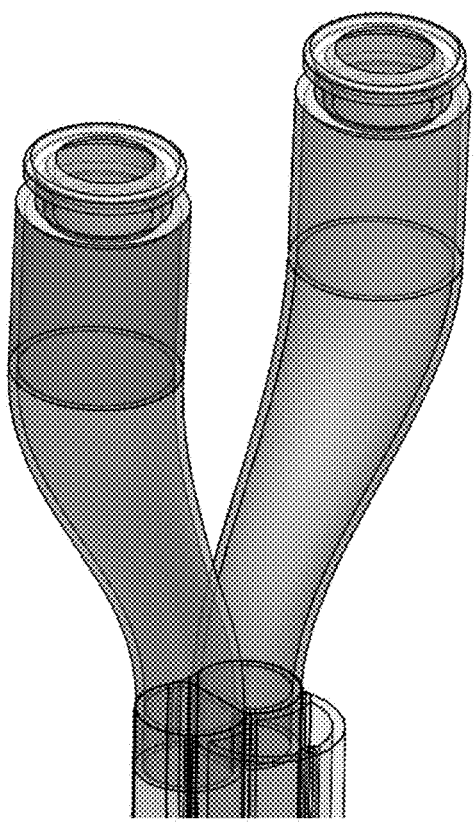
FIG. 32. Suction Port Lids without Secondary Tubes.
Figure 33:
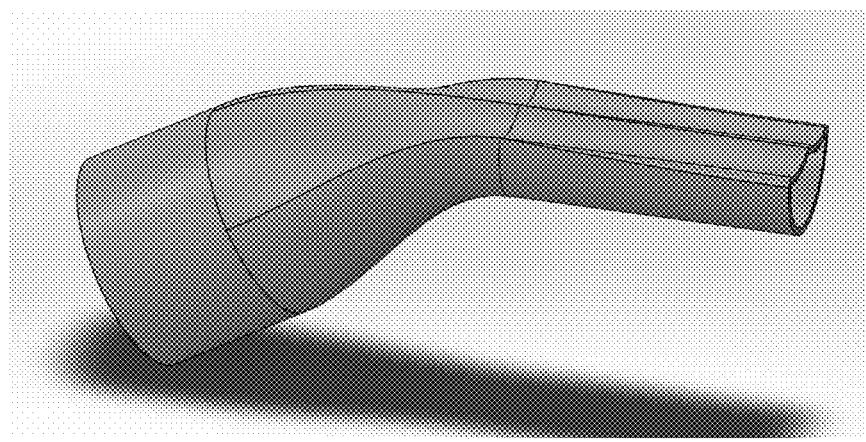
FIG. 33. Primary ventilator connector.
Figure 34A:
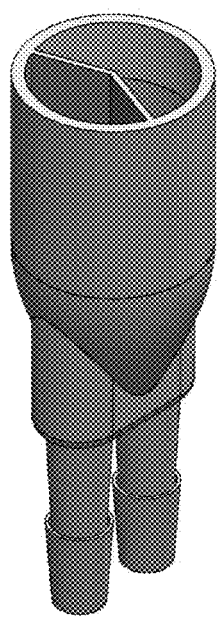
FIGS. 34A-B. (A) Secondary ventilator connector and (B) seal caps.
Figure 34B:
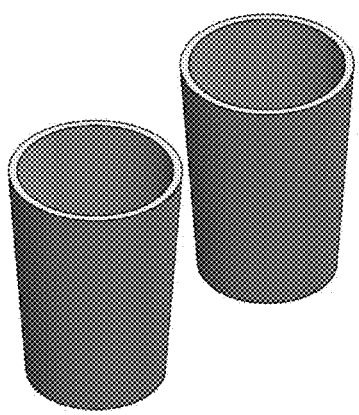

Thin Film:

The thin film lays flat along the primary tube until the secondary tubes are needed. Once the secondary tubes are needed, the tubes are guided through the thin film. There is also a thin film divider in the center to keep the tubes from crossing. (see FIG. 30).

Suction Port Lids:

The flip-top suction ports are an industry standard to keep a potential opening sealed. A standard suction port lid will be locked over the top of the suction port until the secondary tubes are needed. The suction ports have markings to indicate the orientation of the primary tube as well as for the placement of the secondary tubes. Yellow markings are on the left suction port lid, and red markings are on the right suction port lid. If the patient still needs general breathing assistance, replace the port lids to ensure no air leakage.

Primary Ventilator Connector:

The primary ventilator connector is inserted into the primary tube and establishes a 15 mm connection with a ventilator.

Secondary Ventilator Connector:

The secondary connector is inserted into the secondary tubes and connects to the ventilator, using the standard 15 mm connection end. The color markings on the inside of the ventilator side align the connector with the corresponding secondary tubing. The connector has the ability to use either one or both of the secondary tubes. If a second secondary tube is not needed, the seal cap must be used to prevent air from leaking through the second secondary tube opening.

Guidance Vision Tool:

The guidance vision tool will be either a laryngoscope or an endoscope, depending on the tools available and the practitioners preference. A child endoscope is preferred as it will be needed for the placement of the secondary tube(s). The guiding tool will be used to aid in placement of the primary and secondary tubes.

Lubrication:

Lubricant should be applied on the outside of tubing so that tubing may slide easier. Since the secondary and primary tubes are both plastic, the friction is naturally very high. Lubrication will reduce the friction during sliding between these tubes.

Setup Instructions:

Test that the inflation cuffs do inflate by inflating the cuffs and then deflating. This can be achieved by inserting a Luer tip syringe into the Luer connector of the pilot balloon, and injecting air. An inflated pilot balloon indicates that a positive pressure inside the inflation system is sustained.

Power the Guidance Vision Tool.

This will be either a laryngoscope or an endoscope, depending on the tools available as well as preference. A child endoscope is preferred as it is needed for the placement of the secondary tube(s). Confirm that the bulb to vision tool is working.

Figure 35:
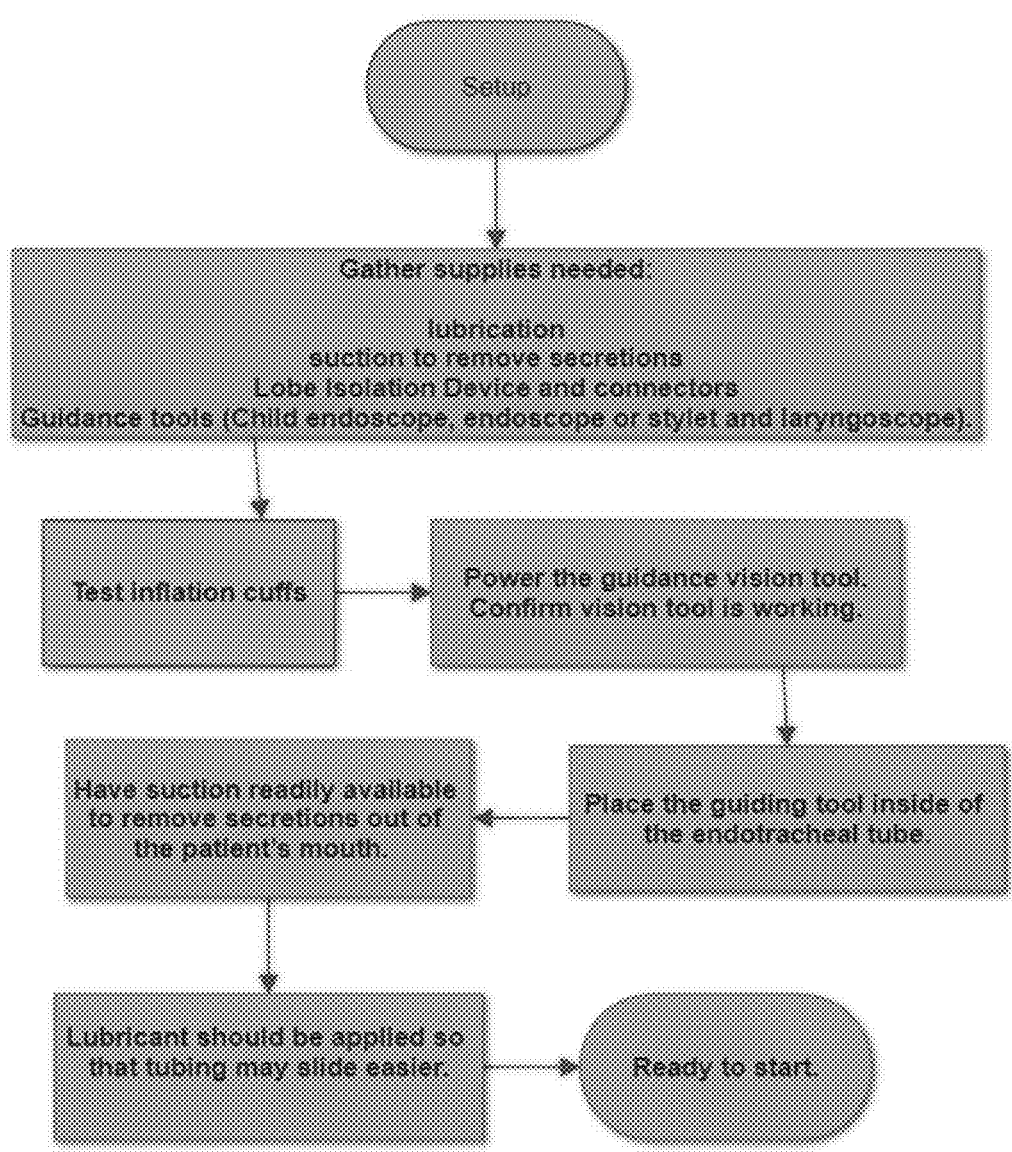
FIG. 35. Set Up Instructions Flow Chart.

Place the guiding tool inside of the endotracheal tube. If the laryngoscope is used, a metal stylet is used to physically guide the device through the trachea. If the endoscope is used, it will function as the guidance and visual tool. Make sure the tip of the guiding tool is recessed from the end of the endotracheal tube to prevent injury. Have a suction device readily available to remove secretions out of the patient's mouth. This prevents fluid from traveling along the walls of the device and into the patient's lungs. Lubricant should be applied to the exterior so that tubing may slide easier. (see FIG. 35)

Figure 36:
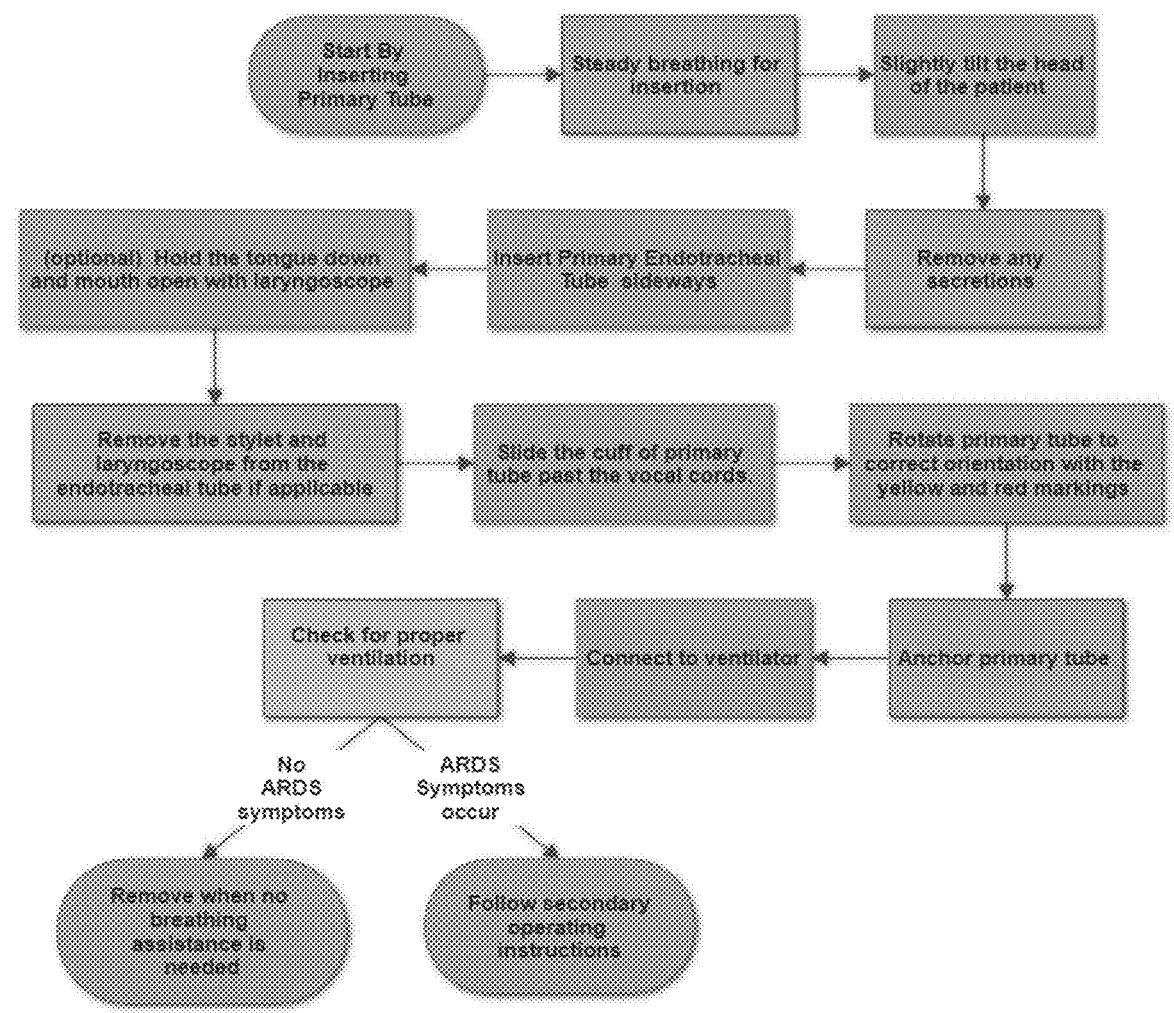
FIG. 36. General Operating Instructions Flow Chart.
Figure 37:
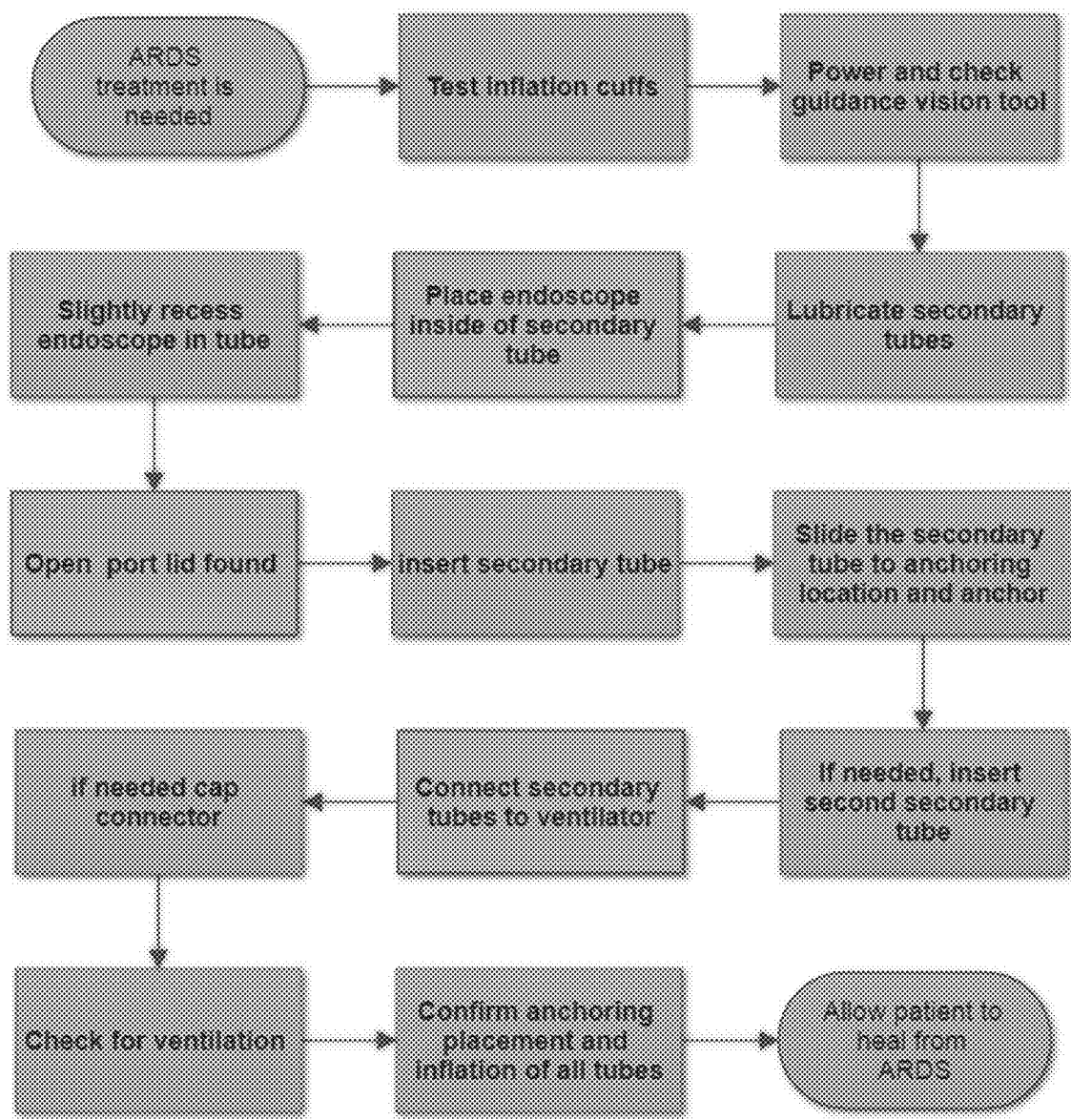
FIG. 37. Secondary Operating Instructions Flow Chart.

General Operating Instructions:

Once setup is complete, synchronize breathing with patient and intubate while both you and the patient are holding the breath. This allows for steadier motion of insertion. Slightly tilt the head of the patient and apply suction to remove secretions from the patient's mouth. The primary endotracheal tube should be tilted 90 degrees so that both Primary tubing and Secondary tubing channel are pointing at either the patient's left or right. (Optional) If the laryngoscope is introduced to hold the tongue out of the way and hold the mouth open, ensure the elevation goes up and away from patient to avoid cranking on the teeth. Once the pharynx is reached, the epiglottis must be passed, by inserting the Primary tubing towards the patient's anterior (on the frontside) to access the trachea (the backside is the esophagus). Visualizing the larynx, slide the cuff past the vocal cords. Once the inflation cuff for the primary tube has passed the vocal cords, make sure the yellow markings are on the left and the red markings are on the right. The markings on the primary tube are found at the top near the flip-top silicon suction port lids. If using a laryngoscope in combination with a stylet, remove the stylet from the endotracheal tube. Inflate the cuff of the primary tube. This anchors the endotracheal tube and creates a pressure seal. Connect the primary ventilator connector to the primary tube by inserting the smaller side into the endotracheal tube until it no longer slides. Then, attach the ventilator to the 15 mm end of the primary ventilator connector. Refer to the ventilator operational manual for further instructions on mechanical ventilation. Check for ventilation by watching for the rise and fall of the patient's chest. Auscultate with a stethoscope to hear normal airflow on both sides of the lungs. The ventilator will monitor and display the end tidal $CO_2$ level to make sure that the tube in inserted inside of the trachea. (see FIG. 36)

Secondary Operating Instructions:

If ARDS symptoms occur and further assistance is needed, the secondary tubes should be used for additional breathing aid. Use sterile unused secondary tubes only. Test the inflation cuffs by inflating the cuffs and then deflating. This can be achieved by inserting a Luer tip syringe into the Luer connector of the pilot balloon, and injecting air. An inflated pilot balloon indicates that a positive pressure inside the inflation system is sustained. Power the guidance vision tool. A child's endoscope is required due to the smaller sized of the secondary tubes. Confirm that the bulb to endoscope is working. Place the child endoscope inside of the secondary tube to be inserted. Either the left or the right secondary tube may be inserted first. The tube with the red markings near the inflation cuff should be used for the right middle and lower lobes. The tube with the yellow markings near the inflation cuff should be used for the left lower lobe. Make sure the tip of the child endoscope is slightly recessed from the end of the endotracheal tube. Lubricant should be applied to the outside of the tube in order to decrease friction while sliding. Open the corresponding flip-top silicon suction port lid found at the top of the endotracheal tube and insert the externally lubricated secondary tube. If using the red secondary tube, insert it in the port lid with red markings. If using the yellow secondary tube, insert it in the port lid with yellow markings. Slide the secondary tube to the designated anchor spot for the corresponding side of the lungs. The secondary tube meant for the left lower lobe should be anchored at the approximate midpoint of the left lower lobar bronchus. The secondary tube meant for the right middle and lower lobes should be anchored after the right upper lobar bronchus but before the right middle lobar bronchus (*Bronchus intermedius*). To anchor the secondary tube insert a Luer tip syringe into the Luer connector of the pilot balloon, and injecting air. This anchors the secondary tube and creates a pressure seal. If both secondary tubes are needed, follow steps to insert the second secondary tube. If the second secondary tube is not needed the seal cap must be placed on the secondary ventilator connector to prevent air from leaking through the second secondary tube opening. Connect the secondary ventilator connector to the corresponding secondary tube by fully inserting the cone shape into the secondary tube(s) until it no longer slides. Make sure to align the connector such that the yellow and red markings correspond to the secondary tubing. Then, attach the ventilator to the 15 mm secondary ventilator connector. Follow the ventilator instructions for further use of the ventilator. Check for functioning ventilation by watching for the rise and fall of the patient's chest. Auscultate with a stethoscope to hear normal airflow on both sides of the lungs. The ventilator will monitor and display the end-tidal capnography. Confirm anchoring placement and inflation is correct for the primary tube and secondary tube(s) inserted.

Figure 38:
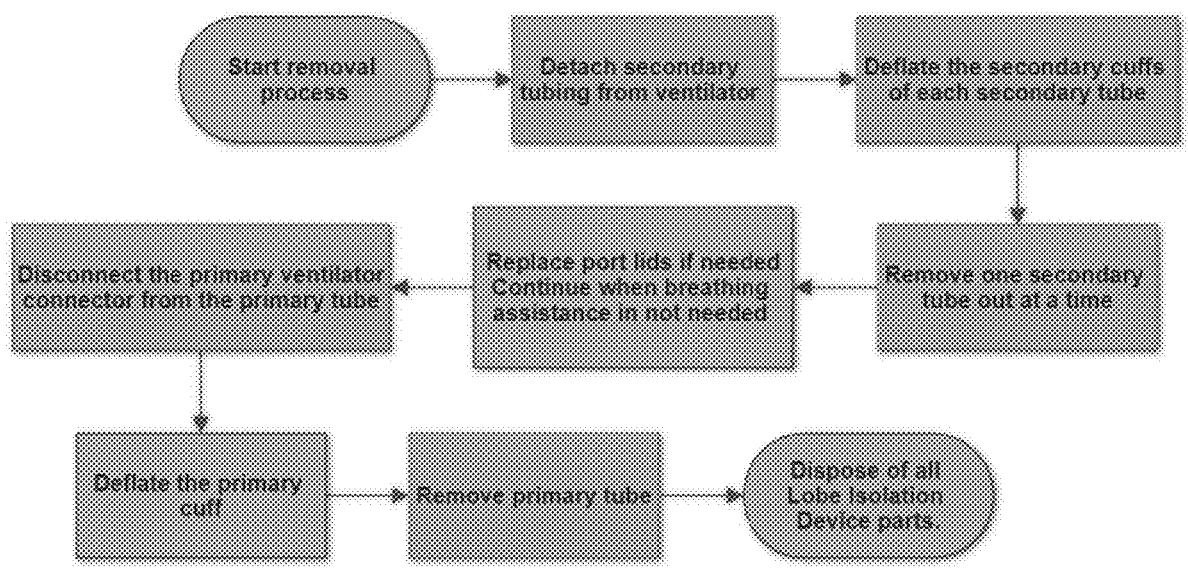
FIG. 38. Removal Instructions Flow Chart.

Removal Instructions:

When the patient no longer needs further assistance breathing and shows recovery from ARDS symptoms, the secondary tubes may be removed. Remove the primary tube from the patient only when no assistance is needed for regular breathing. Remove the secondary ventilator connector from the secondary tube(s). Insert a syringe into the pilot balloon of the secondary tube(s) deep enough to open the one-way valve inside and remove the air. This deflates the cuff and releases the anchoring. Release the anchor before removal of each secondary tube. Gently pull one secondary tube out at a time until only the primary tube is left in the patient. Remove all secondary tubes before beginning of the removal of primary endotracheal tube. Once the patient no longer needs assistance with breathing, disconnect the primary ventilator connector from the primary tube. Insert a syringe into the pilot balloon of the primary tube to open the one-way valve inside and remove the air. This deflates the cuff and releases the anchoring. Gently pull the primary tube out of the patient. Dispose of all Lobe Isolation Device parts. (see FIG. 38)

The invention claimed is:

1. An endotracheal tube assembly comprising:
    (a) an elongated body forming a tracheal tube having (i) a distal end configured to be inserted into a subject's lungs, the tracheal tube forming a tracheal tube lumen configured to access the right upper lobe of the lungs and the left upper lobe of the lungs when in use, (ii) a collapsible insertion guide that forms a collapsible insertion guide lumen along the long axis of the tracheal tube, the insertion guide lumen is configured to receive at least two bronchial tubes, and (iii) a tracheal cuff around the distal tracheal tube portion inserted into the lungs that can be expanded to seal against the trachea, wherein the collapsible insertion guide is positioned outside the tracheal tube portion wall and inside the tracheal cuff;
    (b) a first bronchial tube having a proximal end and a distal end, the distal end being a bronchial portion configured to be inserted into a right intermediate bronchus of the right lung, the first bronchial tube can be assembled with the tracheal tube by insertion through the insertion guide lumen when in use,
    (c) a second bronchial tube having a proximal end and a distal end, the distal end being a bronchial portion configured to be inserted into a left lower bronchus of the left lung, the second bronchial tube can be assembled with the tracheal tube by insertion through the insertion guide lumen when in use;
    wherein the assembly of the tracheal tube, the first bronchial tube, and the second bronchial tube provides three lumens, (i) a first tracheal tube lumen accessing the right upper lobe and the left upper lobe of the lungs and configured to provide ventilation to the upper lobes of the lungs during use, (ii) a first bronchial tube lumen configured to provide ventilation to the right middle lobe and right lower lobe of the lung independent of the tracheal portion, and (iii) a second bronchial tube lumen configured to provide ventilation independent of the tracheal portion to the left lower lobe of the lungs.

2. The endotracheal tube of claim 1, wherein the first bronchial tube, the second bronchial tube, or the first and the second bronchial tubes further comprise a bronchial tube cuff that can be expanded to seal a bronchus.

3. The endotracheal tube of claim 1, wherein the collapsible insertion guide is formed by a thin film attached to the tracheal tube portion.

4. A ventilator system comprising the endotracheal tube assembly of claim 1, wherein the system is configured for asynchronous ventilation of selected lung lobes.

* * * * *